(12) United States Patent
Miller et al.

(10) Patent No.: US 6,512,224 B1
(45) Date of Patent: Jan. 28, 2003

(54) LONGITUDINAL FIELD DRIVEN FIELD ASYMMETRIC ION MOBILITY FILTER AND DETECTION SYSTEM

(75) Inventors: Raanan A. Miller, Cambridge, MA (US); Markus Zahn, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 09/439,543

(22) Filed: Nov. 12, 1999

Related U.S. Application Data

(63) Continuation-in-part of application No. 09/358,312, filed on Jul. 21, 1999.

(51) Int. Cl.[7] .......................... B01D 59/44; H01J 49/00
(52) U.S. Cl. ....................... 250/286; 250/287
(58) Field of Search .................... 250/286, 287, 250/281, 282

(56) References Cited

U.S. PATENT DOCUMENTS

| | | | |
|---|---|---|---|
| 5,420,424 A | 5/1995 | Carnahan et al. | |
| 5,455,417 A | 10/1995 | Sacristan | 250/287 |
| 5,536,939 A | 7/1996 | Freidhoff et al. | 250/281 |
| 5,723,861 A | 3/1998 | Carnahan et al. | 250/287 |
| 5,736,739 A | 4/1998 | Uber et al. | 250/287 |
| 5,763,876 A | 6/1998 | Pertinarides et al. | 250/288 |
| 5,789,745 A | * 8/1998 | Martin | 250/286 |
| 5,801,379 A | 9/1998 | Kouznetsov | 250/286 |
| 5,834,771 A | * 11/1998 | Yoon et al. | 250/286 |
| 5,965,882 A | 10/1999 | Megerle et al. | 250/287 |
| 6,051,832 A | 4/2000 | Bradshaw et al. | 250/286 |

FOREIGN PATENT DOCUMENTS

| | | |
|---|---|---|
| RU | 966583 | 10/1982 |
| RU | 1337934 A2 | 9/1987 |
| RU | 1405489 A1 | 6/1998 |
| RU | 1412447 A1 | 6/1998 |
| RU | 1485808 | 6/1998 |
| RU | 1627984 A2 | 7/1998 |
| WO | WO 00/08454 | 8/1999 |
| WO | WO 00/08456 | 8/1999 |
| WO | WO 00/08457 | 8/1999 |
| WO | WO 00/08455 | 2/2000 |
| WO | WO 01/08197 A1 | 2/2001 |

OTHER PUBLICATIONS

Buryakov, et al., *Separation of ions accordings to mobility in a strong ac electric field*, 1991 American Institute of Physics, Sov. Tech. Phys. Lett. 17(6), Jun. 1991, pp. 446–447.

Carnahan, et al., *Field Ion Spectrometry—A New Analytical Technology for Trace Gas Analysis*, ISA 1996—Paper #96–009, pp. 87–96.

Buryakov et al., *A new method of separation of multi–atomic ions by mobility at atmospheric pressure using a high–frequency amplitude–asymmetric strong electric field*, 1993, International Journal of Mass Spectrometry and Ion Processes 128, pp. 143–148.

(List continued on next page.)

*Primary Examiner*—Bruce C. Anderson
(74) *Attorney, Agent, or Firm*—Hamilton, Brook, Smith & Reynolds, P.C.

(57) ABSTRACT

An asymmetric field ion mobility spectrometer with an ionization source for ionizing a sample media and creating ions. An ion filter is disposed in the analytical gap downstream from the ionization source for creating an asymmetric electric field to filter the ions. An ion flow generator for creating an electric field in a direction transverse to the asymmetric electric field and which propels the ions through the asymmetric electric field towards a detector.

14 Claims, 22 Drawing Sheets

OTHER PUBLICATIONS

Russell Handy et al. "Determination of Nanomolar Levels of Perchlorate in Water by ESI–FAIMS–MS", Journal of Analytical Atomic Spectrometry, vol. 15 No. 8, p. 907–911, Aug. 2000.

I.A. Burykov, et al., "Device And Method For Gas Electrophoresis," *Chemical Analysis of Environment*, edit. Prof. V.V. Malakhov, Novosibirsk: Nauka, 1991, p. 113–127.

A.N. Verenchikov, et al., "Analysis Of Ionic Composition Of Solutions Using An Ion Gas Analyzer," *Chemical Analysis of Environment*, edit. Prof. V.V. Malakhov, Novosibirsk: Nauka, 1991, pp. 127–134.

Buryakov, I.A. et al., "Drift Spectrometer for the Control of Amine Traces in the Atmosphere," *J. Analytical Chem.* 48(1):156–165 (1993). Appears to be English translation of attached Russian reference (Zhurnal Anal. Chim., 48:N1, p. 156 (1993)).

Guevremont, Roger and Purves, Randy W., "High Field Asymmetric Waveform Ion Mobility Spectrometry–Mass Spectrometry: An Investigation of Leucine Enkephalin Ions Produced by Electrospray Ionization," *J. Am. Soc. Mass. Spectrom.* 10:492–501 (1999).

Handy, Russell et al., "Determination of nanomolar levels of perchlorate in water by ESI–FAIMS–MS," *JAAS* 15:907–911 (2000).

Miller, R.A. et al., "A Novel Micromachined High–Field Asymmetric Waveform Ioon Mobility Spectrometer," Dept of Chem. And Biochem., New Mexico State University, Oct. 10, 1999.

Verenchikov, A.N. et al., Analysis ions in solutes by gaseous ion analyzer. "Chemical Analysis of the Environmental Objects," red. Malakhov. Novosibirsk, Nauka, pp. 127–134 (1991).

Buryakov, I.A. et al., Devices and Methods of the Gaseous Electrophoresis. "Chemical Analysis of the Environmental Objects," red. Malakhov. Novosibirsk, Nauka, pp. 113–127 (1991).

Buryakov, I.A. et al., "Separation Ions According to Mobility in a Strong ac electric Field," *Sov. Tech. Phys. Lett.* 17(6):446–447 (1991). Appears to be English translation of attached Russian reference (Pisma v ZTF, v.17, N12, p. 60 (1991)).

* cited by examiner

LONGITUDINAL FIELD DRIVEN FIELD ASYMMETRIC ION MOBILITY FILTER AND DETECTION SYSTEM

RELATED CASES

This application is a Continuation-In-Part Application of application Ser. No. 09/358,312 filed Jul. 21, 1999.

FIELD OF INVENTION

This invention relates to a Longitudinal Field Driven Field Asymmetric Ion Mobility (FAIM) filter, and more particularly to a micromachined spectrometer.

BACKGROUND OF INVENTION

The ability to detect and identify explosives, drugs, chemical and biological agents as well as air quality has become increasingly more critical given increasing terrorist and military activities and environmental concerns. Previous detection of such agents was accomplished with conventional mass spectrometers, time of flight ion mobility spectrometers and conventionally machined FAIM spectrometers.

Mass spectrometers are very sensitive, highly selective and provide a fast response time. Mass spectrometers, however, are large and require significant amounts of power to operate. They also require a powerful vacuum pump to maintain a high vacuum in order to isolate the ions from neutral molecules and permit detection of the selected ions, and are also very expensive.

Another spectrometric technique which is less complex is time of flight ion mobility spectrometry which is the method currently implemented in most portable chemical weapons and explosives detectors. The detection is based not solely on mass, but on charge and cross-section of the molecule as well. However, because of these different characteristics, molecular species identification is not as conclusive and accurate as the mass spectrometer. Time of flight ion mobility spectrometers typically have unacceptable resolution and sensitivity limitations when attempting to reduce their size, that is a drift tube length less than 2 inches. In time of flight ion mobility, the resolution is proportional to the length of the drift tube. The longer the tube the better the resolution, provided the drift tube is also wide enough to prevent all ions from being lost to the side walls due to diffusion. Thus, fundamentally, miniaturization of time of flight ion mobility systems leads to a degradation in system performance. While conventional time of flight devices are relatively inexpensive and reliable, they suffer from several limitations. First, the sample volume through the detector is small, so to increase spectrometer sensitivity either the detector electronics must have extremely high sensitivity, requiring expensive electronics, or a concentrator is required, adding to system complexity. In addition, a gate and gating electronics are usually needed to control the injection of ions into the drift tube.

FAIM spectrometry was developed in the former Soviet Union in the 1980's. FAIM spectrometry allows a selected ion to pass through a filter while blocking the passage of undesirable ions. One prior FAIM spectrometer was large and expensive, e.g., the entire device was nearly a cubic foot in size and cost over $25,000. These systems are not suitable for use in applications requiring small detectors. They are also relatively slow, taking as much as one minute to produce a complete spectrum of the sample gas, are difficult to manufacture and are not mass producible.

Moreover, the pumps required to draw a sample medium into the spectrometer and to provide a carrier gas can be rather large and consume large amounts of power. And, the carrier gas necessarily must flow in the same direction as the ions which requires a structure which separates the analytical gap from the ionization source.

BRIEF SUMMARY OF THE INVENTION

It is therefore an object of this invention to provide a FAIM filter and detection system which can more quickly and accurately control the flow of selected ions to produce a sample spectrum than conventional FAIM devices.

It is a further object of this invention to provide such a filter and detection system which can detect multiple preselected ions without having to sweep the bias voltage.

It is a further object of this invention to provide such a filter and detection system which can even detect selected ions without a bias voltage.

It is a further object of this invention to provide such a filter and detection system which can detect ions spatially based on the ions' trajectories.

It is a further object of this invention to provide such a filter and detection system which has a very high resolution.

It is a further object of this invention to provide such a filter and detection system which can detect selected ions faster than conventional detection devices.

It is a further object of this invention to provide such a filter and detection system which has a sensitivity of parts per billion to parts per trillion.

It is a further object of this invention to provide such a filter and detection system which may be packaged in a single chip.

It is a further object of this invention to provide such a filter and detection system which is cost effective to implement and produce.

It is a further object of this invention to provide such a filter and detection system which does not require the high flow rate, high power consumption pumps normally associated with spectrometers.

This invention results from the realization that the pumps used to draw a sample media such as a gas into a FAIM spectrometer and to provide a flow of carrier gas can be made smaller or even eliminated in part by the incorporation of an ion flow generator which creates a longitudinal electric field in the direction of the intended ion travel path to propel the ions to the detector and through the transversely directed asymmetric electric field which acts as an ion filter.

The result is the ability to incorporate lower cost, lower flow rate, and smaller, even micromachined pumps; a decrease in power usage; the ability to now apply clean filtered gas (e.g., dehumidified air) in a direction opposite the direction of ion travel to eliminate ion clustering and the sensitivity of the spectrometer to humidity. Separate flow paths for the source gas and the clean filtered gas are no longer required thus reducing the structure required to maintain separate flow paths taught by the prior art. Moreover, if an electrospray nozzle is used as the ionization source, the electrodes used to create the fine droplets of solvent can be eliminated because the electrodes which create the longitudinal and transverse electric fields function to both transport the ions and to create the fine spray of solvent droplets.

The spectrometer can be made extremely small, if required, and used in chemical and military applications, as a filter for a mass spectrometer, as a detector for a gas chromatograph, as a front end to a time of flight ion mobility spectrometer for increased resolution or as a filter for a flexural plate wave device.

The invention results from the further realization that an extremely small, accurate and fast FAIM filter and detection system can be achieved by defining a flow path between a sample inlet and an outlet using a pair of spaced substrates and disposing an ion filter within the flow path, the filter including a pair of spaced electrodes, one electrode associated with each substrate and a controller for selectively applying a bias voltage and an asymmetric periodic voltage across the electrodes to control the path of ions through the filter.

The invention results from the further realization that by providing an array of filters, each filter associated with a different bias voltage, the filter may be used to detect multiple selected ions without sweeping the bias voltage.

The invention results from the further realization that by varying the duty cycle of the periodic voltage, no bias voltage is required.

The invention results from the further realization that by segmenting the detector, ion detection may be achieved with greater accuracy and resolution by detecting ions spatially according to the ions' trajectories as the ions exit the filter.

This invention features an ion mobility spectrometer comprising an ionization source for ionizing a sample media and creating ions; an analytical gap; an ion filter disposed in the analytical gap downstream from the ionization source for creating an asymmetric electric field to filter the ions; an ion flow generator for creating an-electric field in a direction transverse to the asymmetric electric field which is in the longitudinal direction for propelling ions through the asymmetric electric field; and an ion detector for sensing ions not filtered by the ion filter.

The ion detector is typically located proximate to the ion flow generator. The spectrometer may be a radiation source, an ultraviolet lamp, a corona discharge device, or an electrospray nozzle.

The ion filter is preferably connected to an electric controller for applying a bias voltage and an asymmetric periodic voltage to the ion filter. The ion filter typically includes a pair of spaced electrodes for creating an asymmetric electric field between them. The ion flow generator typically includes a plurality of spaced discrete electrodes insulated from these electrodes for creating the transverse direction electric field which propels the ions through the asymmetric electric field and to the detector.

Alternatively, the ion flow generator includes spaced resistive layers and a voltage is applied along each layer to create the longitudinally directed electric field which propels the ions through the asymmetric electric field and to the detector.

In another embodiment, the ion filter includes a first plurality of discrete electrodes electrically connected to an electric controller which applies an asymmetric periodic voltage to them. The ion flow generator includes a second plurality of discrete electrodes dispersed among the electrodes of the ion filter and connected to a voltage source which applies a potential gradient along the second plurality of discrete electrodes.

The analytical gap typically is enclosed by a housing. The ion filter includes electrodes on an inside surface of the housing and the ion flow generator includes electrodes proximate but insulated with respect to the ion filter electrodes. The ion detector also includes electrodes on an inside surface of the housing proximate to the ion filter and the ion flow generator.

The analytical gap is typically enclosed by a housing, the ion filter may include electrodes on an outside surface of the housing and the ion flow generator then includes resistive layers on an inside surface of the housing. A voltage is applied along each resistive layer to create a longitudinal electric field. Alternatively, the ion filter and the ion flow generator are combined and include a series of discrete conductive elements each excited by a voltage source at a different phase.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1:
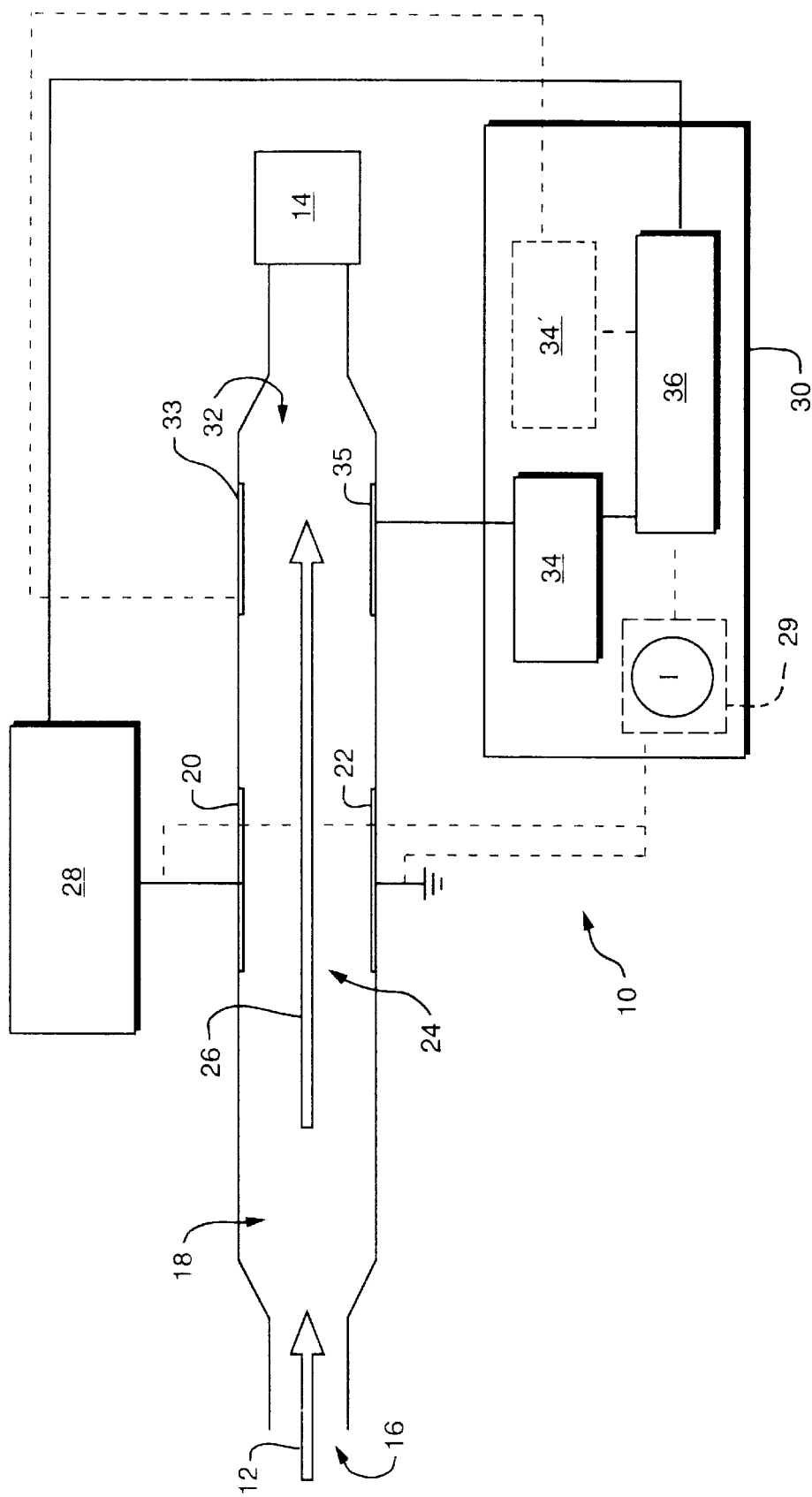
FIG. 1 is a schematic block diagram of the micromachined filter and detection system according to the present invention.

FAIM spectrometer 10, FIG. 1, operates by drawing a gas, indicated by arrow 12, via pump 14, through inlet 16 into ionization region 18. The ionized gas is passed between parallel electrode plates 20 and 22, which comprise ion filter 24, following flow path 26. As the gas ions pass between plates 20 and 22, they are exposed to an electric field between electrode plates 20 and 22 induced by a voltage applied to the plates by voltage generator 28 in response to electronic controller 30. The electric field produced preferably is asymmetric and oscillates in time.

As ions pass through filter 24, some are neutralized by plates 20 and 22 while others pass through and are sensed by detector 32. Detector 32 includes a top electrode 33 at a predetermined voltage and a bottom electrode 35, typically at ground. Top electrode 33 deflects ions downward to electrode 35. However, either electrode may detect ions depending on the ion and the voltage applied to the electrodes. Moreover, multiple ions may be detected by using top electrode 33 as one detector and bottom electrode 35 as a second detector. Electronic controller 30 may include, for example, amplifier 34 and microprocessor 36. Amplifier 34 amplifies the output of detector 32, which is a function of the charge collected by electrode 35 and provides the output to microprocessor 36 for analysis. Similarly, amplifier 34', shown in phantom, may be provided where electrode 33 is also utilized as a detector.

Figure 2:
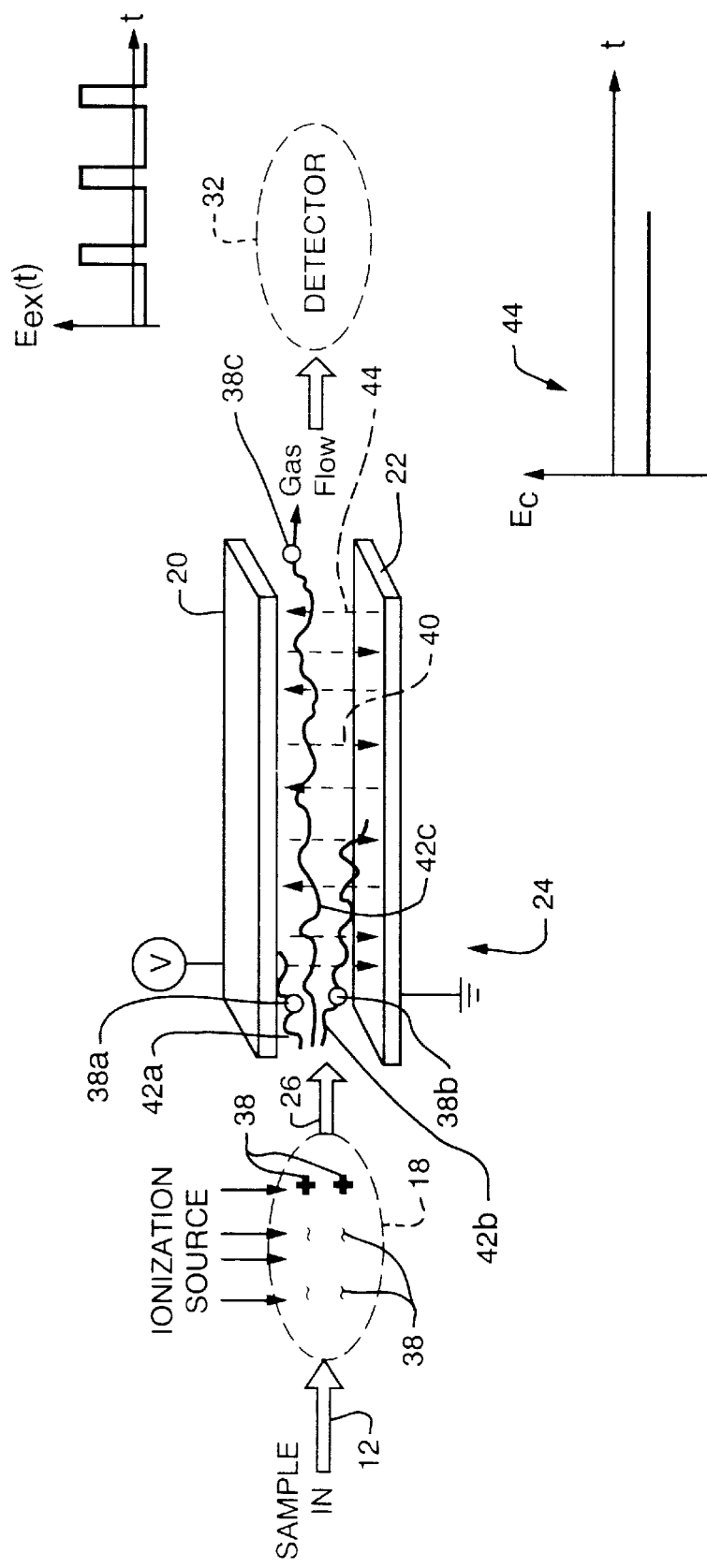
FIG. 2 is a schematic representation of the ions as they pass through the filter electrodes of FIG. 1 toward the detector.

As ions 38, FIG. 2, pass through alternating asymmetric electric field 40, which is transverse to gas flow 12, electric field 40 causes the ions to "wiggle" along paths 42a, 42b and 42c. Time varying voltage V is typically in the range of ±(1000–2000) volts and creates electric field 40 with a maximum field strength of 40,000 V/cm. The path taken by a particular ion is a function of its mass, size, cross-section and charge. Once an ion reaches electrode 20 or 22, it is neutralized. A second, bias or compensation field 44, typically in the range of ±2000 V/cm due to a ±100 volt dc voltage, is concurrently induced between electrodes 20 and 22 by a bias voltage applied to plates 20 and 22, also by voltage generator 28, FIG. 1, in response to microprocessor 36 to enable a preselected ion species to pass through filter 24 to detector 32. Compensation field 44 is a constant bias which offsets alternating asymmetric field 40 to allow the preselected ions, such as ion 38c to pass to detector 32. Thus, with the proper bias voltage, a particular species of ion will follow path 42c while undesirable ions will follow paths 42a and 42b to be neutralized as they encounter electrode plates 20 and 22.

Figure 3A:
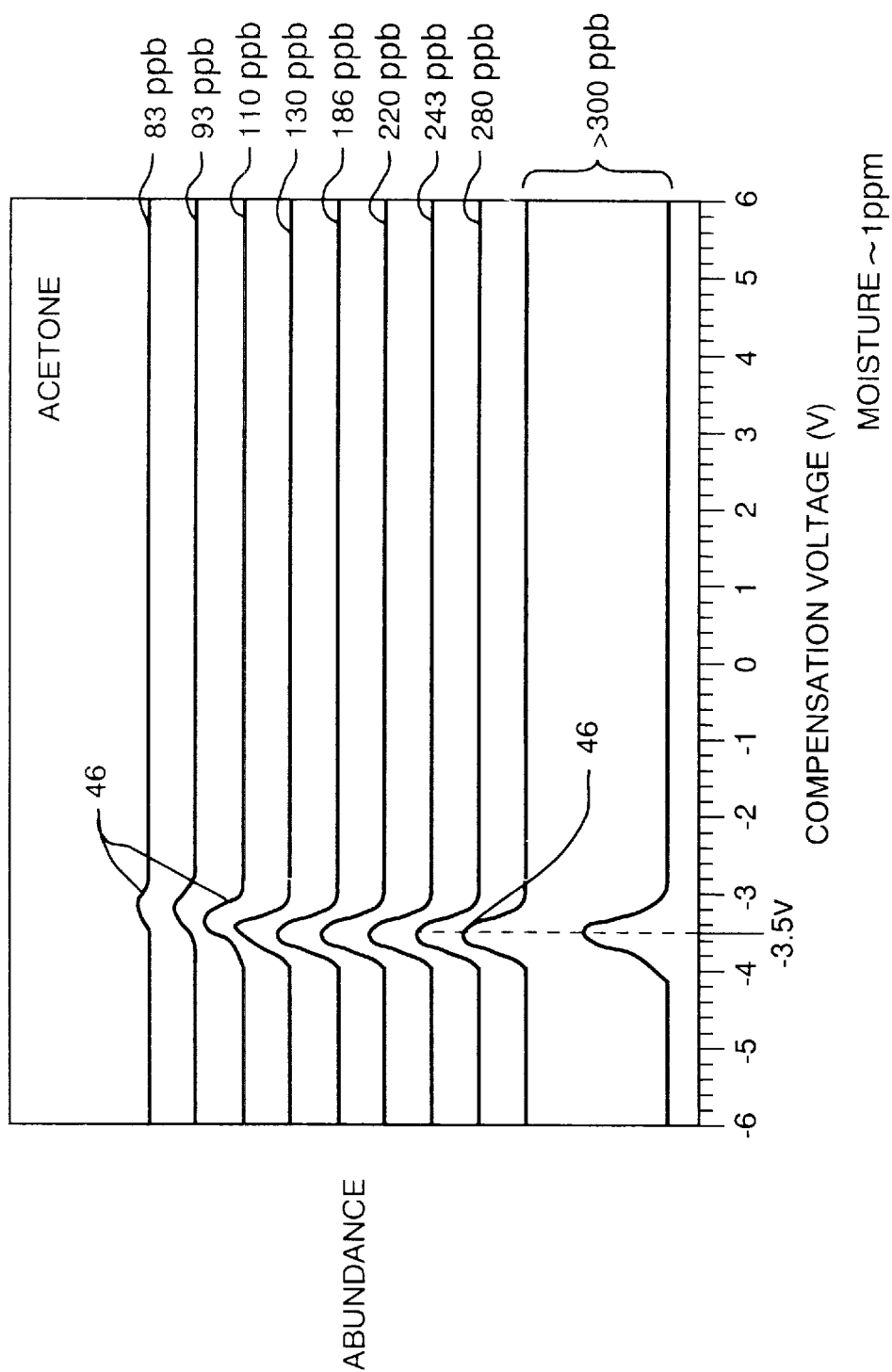
FIG. 3A is a graphical representation of the bias voltage required to detect acetone and the sensitivity obtainable.
Figure 3B:
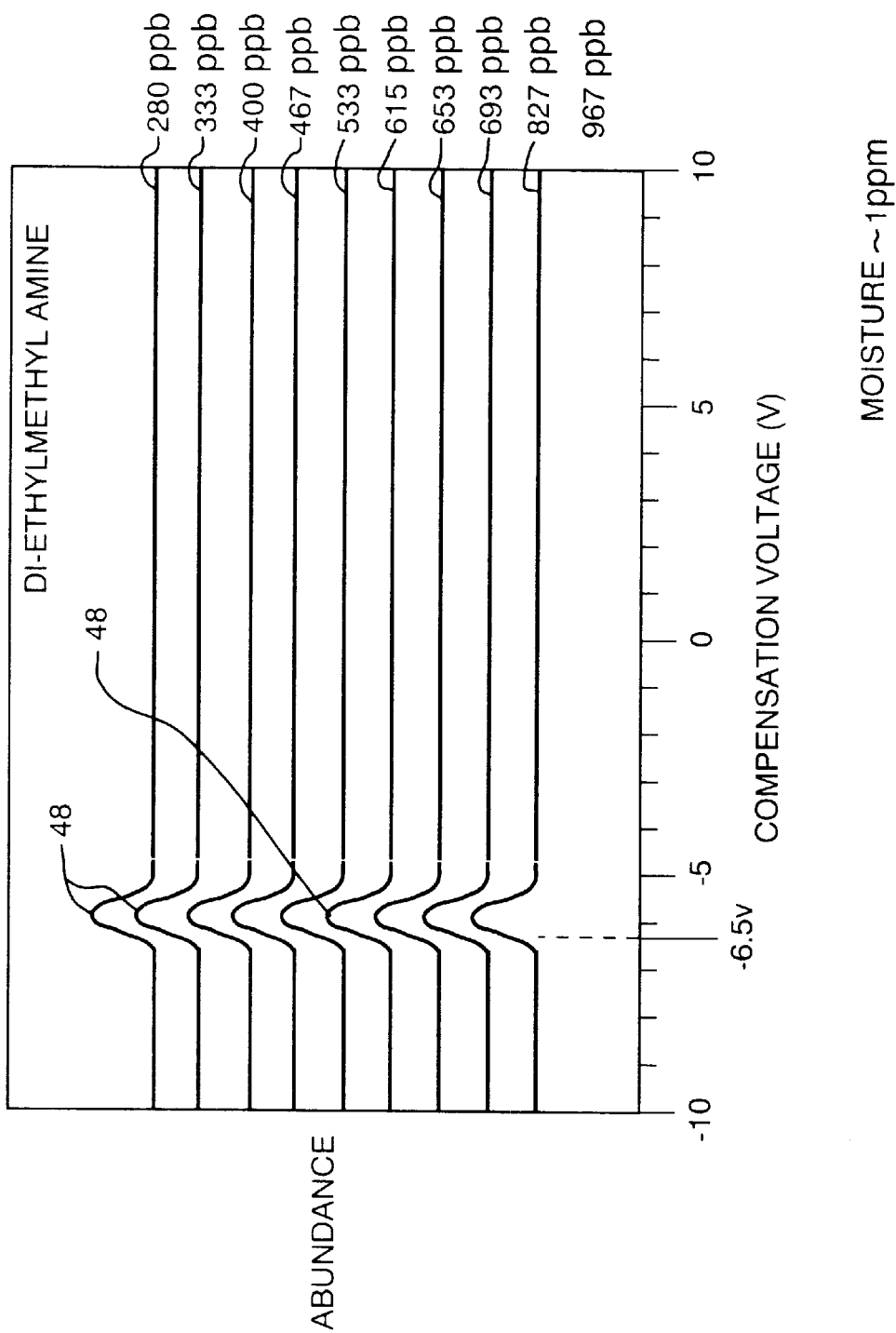
FIG. 3B is a representation, similar to FIG. 3A, of the bias voltage required to detect Diethyl methyl amine.

The output of FAIM spectrometer 10 is a measure of the amount of charge on detector 32 for a given bias electric field 44. The longer the filter 24 is set at a given compensation bias voltage, the more charge will accumulate on detector 32. However, by sweeping compensation voltage 44 over a predetermined voltage range, a complete spectrum for sample gas 12 can be achieved. The FAIM spectrometer according to the present invention requires typically less than thirty seconds and as little as one second to produce a complete spectrum for a given gas sample. By varying compensation bias voltage 44 the species to be detected can be varied to provide a complete spectrum of the gas sample. For example, with a bias voltage of −3.5 volts acetone was detected as demonstrated by concentration peaks 46, FIG. 3A in concentrations as low as 83 parts per billion. In contrast, at a bias voltage of −6.5 volts, diethyl methyl amine, peaks 48, FIG. 3B, was detected in concentrations as low as 280 parts per billion.

Figure 4:
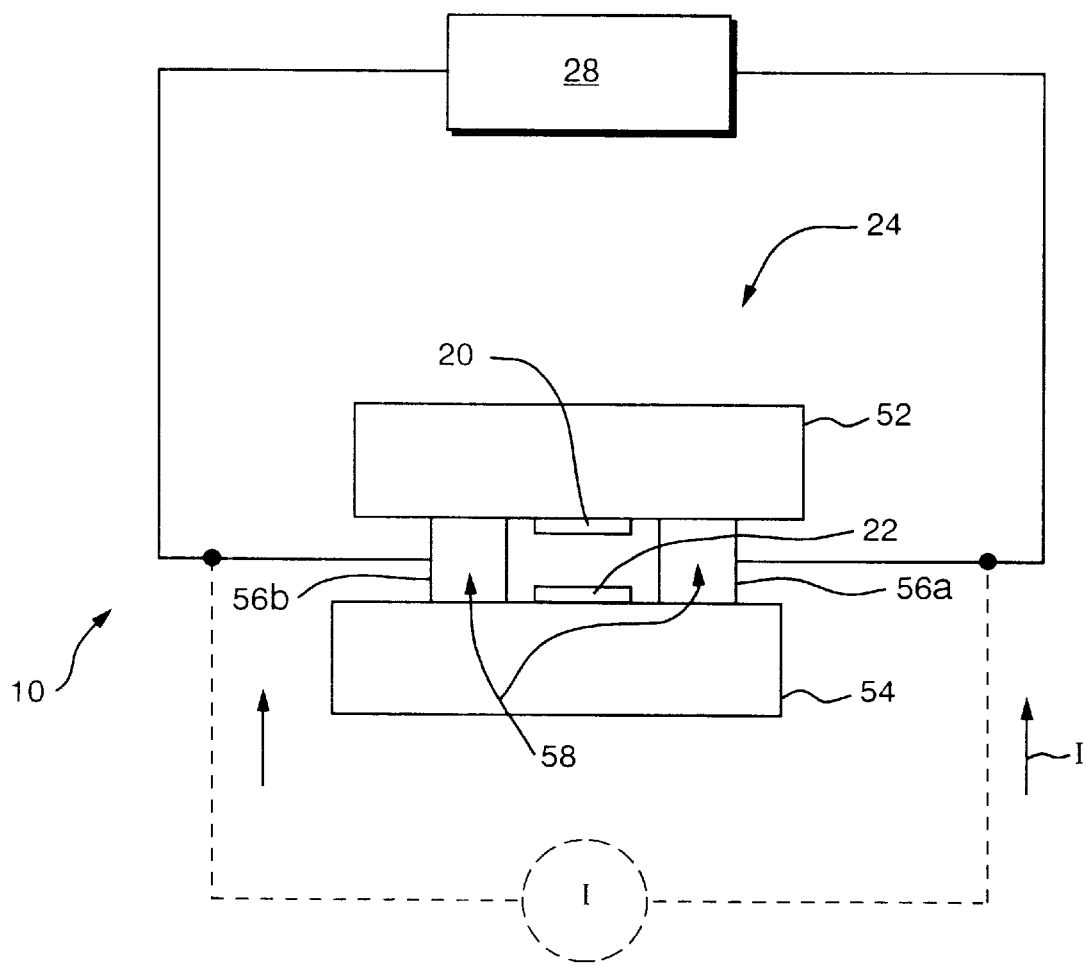
FIG. 4 is a cross sectional view of the spaced, micromachined filter according to the present invention.

Filter 24, FIG. 4, is on the order of one inch in size. Spectrometer 10 includes spaced substrates 52 and 54, for example glass such as Pyrex® available from Corning Glass, Corning, N.Y., and electrodes 20 and 22, which may be for example gold, titanium, or platinum, mounted or formed on substrates 52 and 54, respectively. Substrates 52 and 54 are separated by spacers 56a and 56b which may be formed by etching or dicing silicon wafer. The thickness of spacers 56a–b defines the distance between electrodes 20 and 22. Moreover, applying the same voltage to silicon spacers 56a–b, typically ±(10–1000 volts dc) transforms spacers 56a and 56b into electrodes which can produce a confining electric field 58, which guides or confines the ions' paths to the center of flow path 26, FIG. 1, in order to obtain a better sample spectrum. To confine the ions, spacer electrodes 56a–b must be set to the appropriate voltages so as to "push" the ions to the center of flow path 26. This increases the sensitivity of the system by preserving more ions so that more ions strike electrodes 33 and 35. However, this is not a necessary limitation of the invention.

To maintain accurate and reliable operation of spectrometer 10, neutralized ions which accumulate on electrode plates 20 and 22 must be purged. This may be accomplished by heating flow path 26. For example, controller 30, FIG. 1, may include current source 29, shown in phantom, which provides, in response to microprocessor 36, a current I to electrode plates 20 and 22 to heat the plates, removing accumulated molecules. Similarly, current I may instead be applied to spacer electrodes 56a and 56b, FIG. 4, to heat flow path 26 and clean plates 20 and 22.

Figure 5:
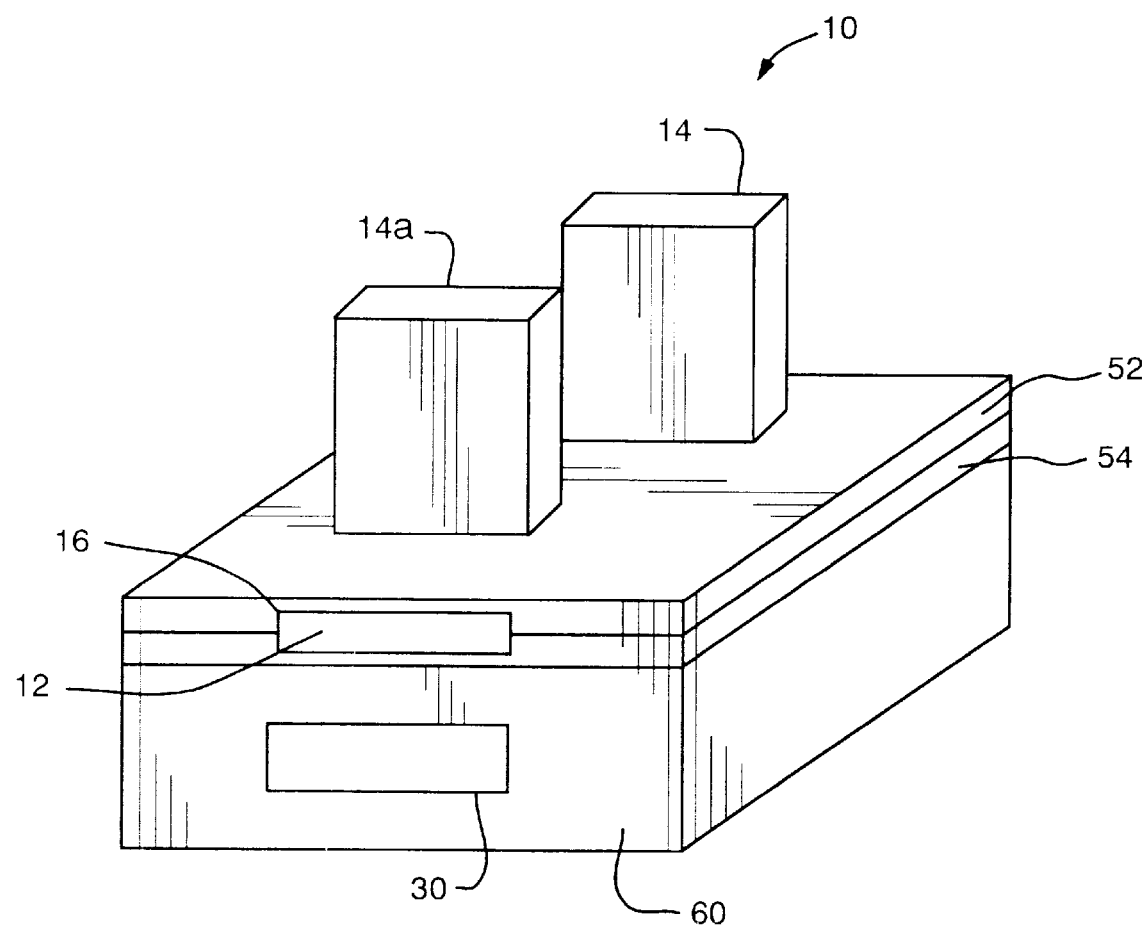
FIG. 5 is a three dimensional view of the packaged micromachined filter and detection system, including fluid flow pumps, demonstrating the miniaturized size which may be realized.

Packaged FAIM spectrometer 10, FIG. 5, may be reduced in size to one inch by one inch by one inch. Pump 14 is mounted on substrate 52 for drawing a gas sample 12 into inlet 16. Clean dry air may be introduced into flow path 26, FIG. 1, by recirculation pump 14a prior to or after ionization of the gas sample. Electronic controller 30 may be etched into silicon control layer 60 which combines with substrates 52 and 54 to form a housing for spectrometer 10. Substrates 52 and 54 and control layer 60 may be bonded together, for example, using anodic bonding, to provide an extremely small FAIM spectrometer. Micro pumps 14 and 14a provide a high volume throughput which further expedites the analysis of gas sample 12. Pumps 14 and 14a may be, for example, conventional miniature disk drive motors fitted with small centrifugal air compressor rotors or micromachined pumps, which produce flow rates of 1 to 4 liters per minute. One example of pump 14 is available from Sensidyne, Inc., Clearwater, Fla.

Figure 6:
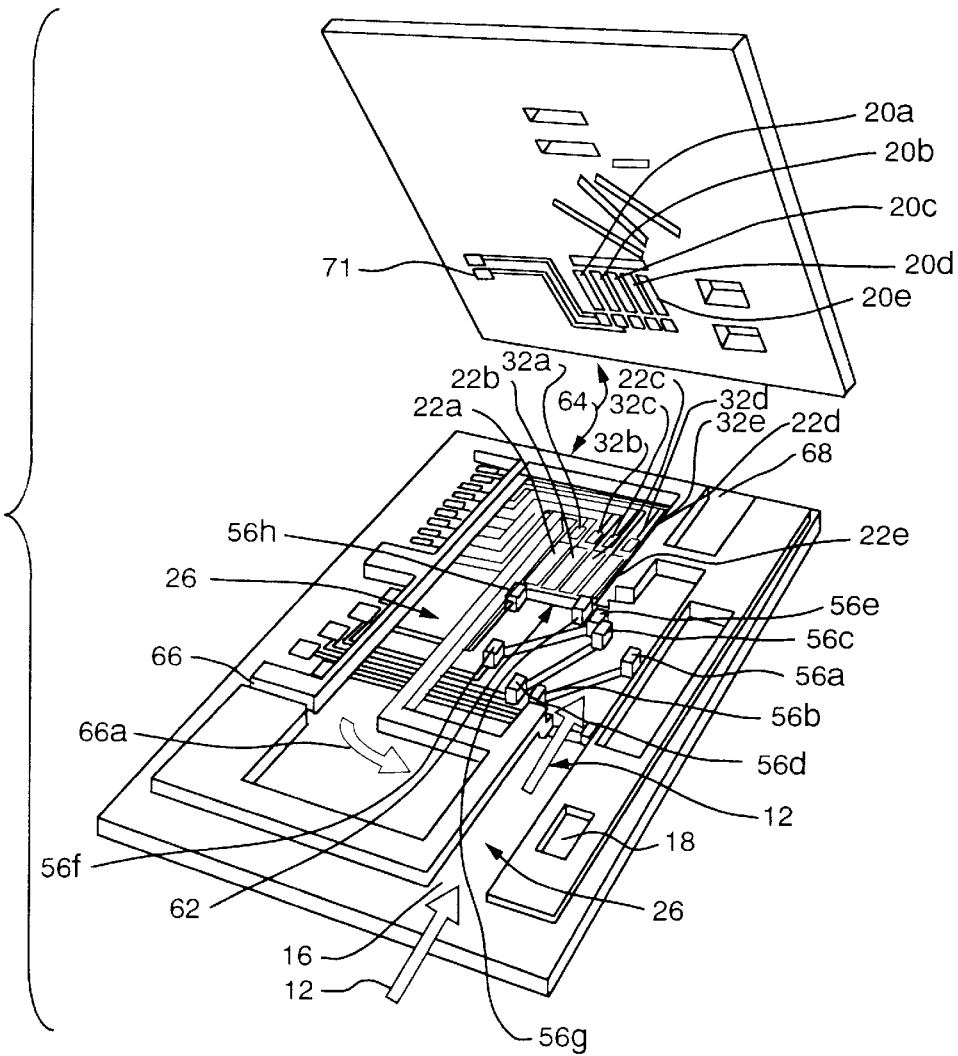
FIG. 6 is an exploded view of one embodiment according to the present invention in which an array of filters and detectors are disposed in the same flow path.

While the FAIM spectrometer according to the present invention quickly produces a spectrum for a particular gas sample, the time for doing so may be further reduced with an array of filters 32. FAIM spectrometer 10, FIG. 6, may include filter array 62, a single inlet 16 and single flow path 26. Sample gas 12 is guided by confining electrodes 56a–h to filter array 62 after passing by ionization source 18, which may include an ultraviolet light source, a radioactive device or corona discharge device. Filter array 62 includes, for example, paired filter electrodes 20a–e and 22a–e and may simultaneously detect different ion species by applying a different compensation bias field 44, FIG. 2, to each electrode pair and sweeping each electrode pair over a different voltage range greatly reducing the sweep time. However, array 62 may include any number of filters depending on the size of the spectrometer. Detector array 64, which includes detectors 32a–e, detects multiple selected ion species simultaneously, thereby reducing the time necessary to obtain a spectrum of the gas sample 12. The electrode pairs share the same asymmetric periodic ac voltage 40.

Clean dry air may be introduced into flow path 26 through clean air inlet 66 via recirculator pump 14a, FIG. 5. Drawing in clean dry air assists in reducing the FAIM spectrometer's sensitivity to humidity. Moreover, if the spectrometer is operated without clean dry air and a known gas sample is introduced into the device, the device can be used as a humidity sensor since the resulting spectrum will change with moisture concentration from the standardized spectrum for the given sample.

Figure 7:
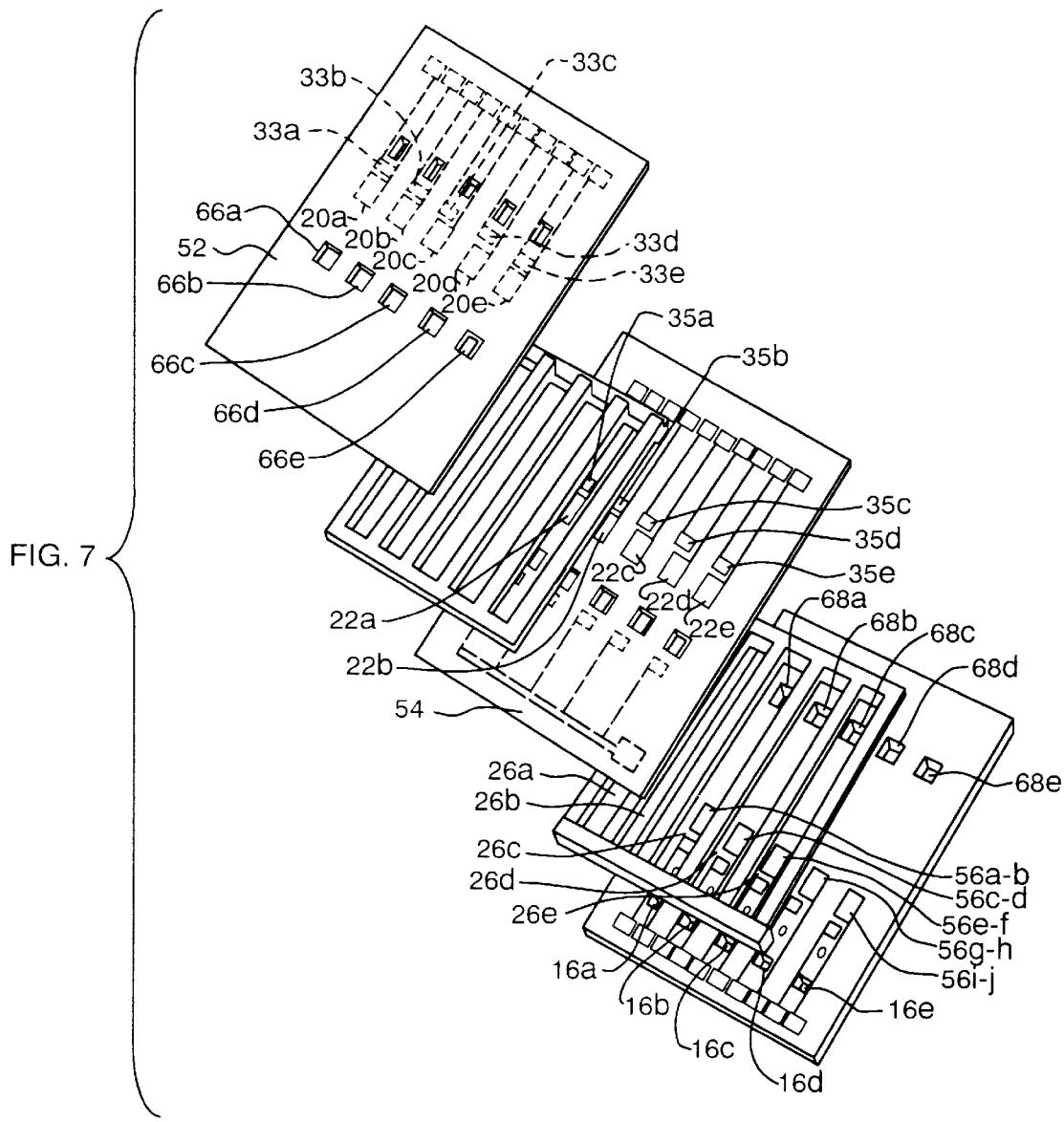
FIG. 7 is an exploded view, similar to FIG. 6, in which the array of filters is stacked and one filter and detector is associated with a single flow path.

However, rather than each filter 32a–e of filter array 62 sharing the same flow path 26, individual flow paths 26a–e, FIG. 7, may be provided so that each flow path has associated with it, for example, inlet 16a, ionization region 18a, confining electrodes 56a', 56b', ion filter electrode pair 20a, 22a, detector electrode pair 33a, 35a and exit port 68a.

Figure 8:
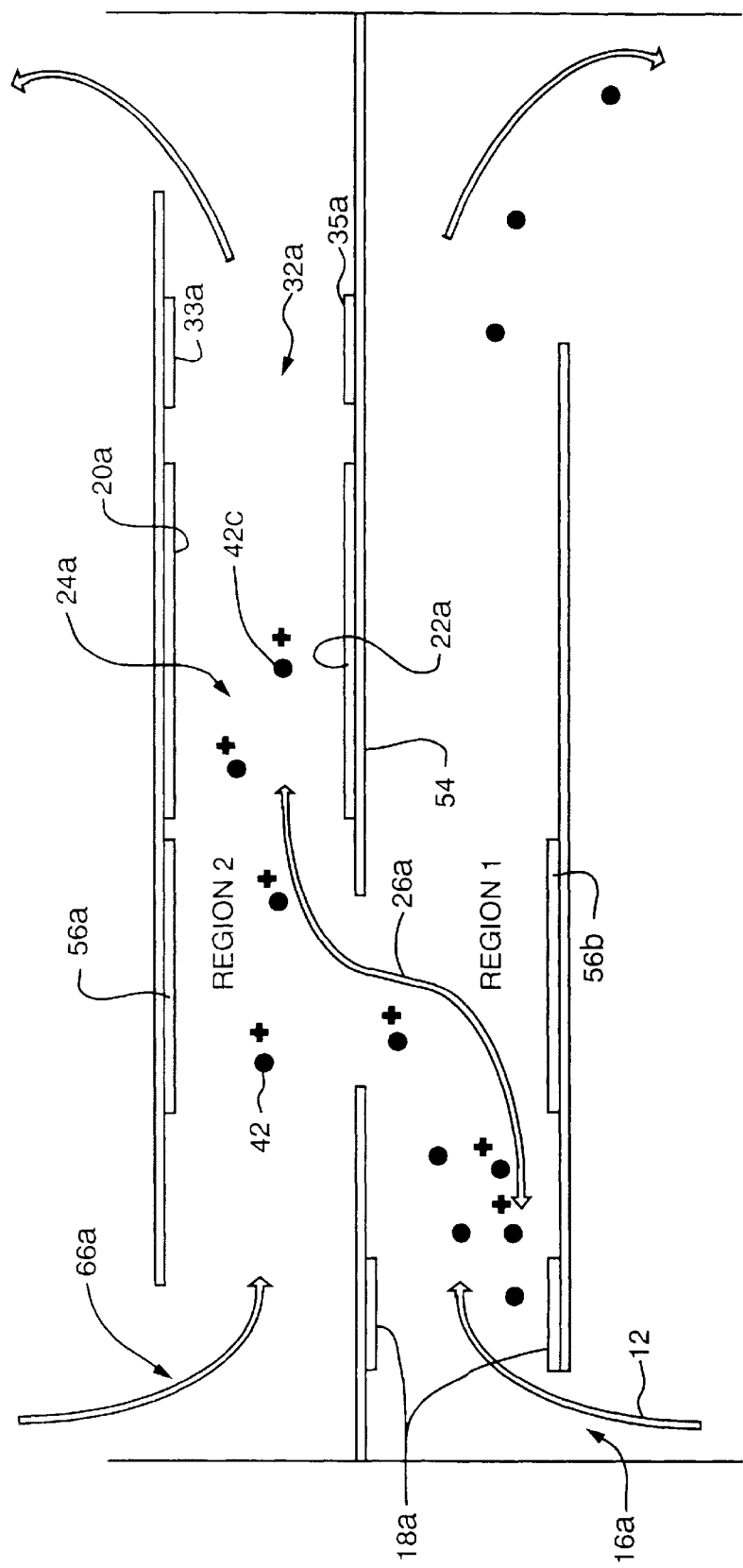
FIG. 8 is a cross sectional representation of a single flow path of the arrayed filter and detector system of FIG. 7.

In operation, sample gas 12 enters sample inlet 16a, FIG. 8, and is ionized by, for example, a corona discharge device 18a. The ionized sample is guided towards ion filter 24a by confining electrodes 56a and 56b. As ions pass between ion filter electrodes 20a and 22a, undesirable ions will be neutralized while selected ions will pass through filter 24a to be detected by detector 32a.

Figure 9:
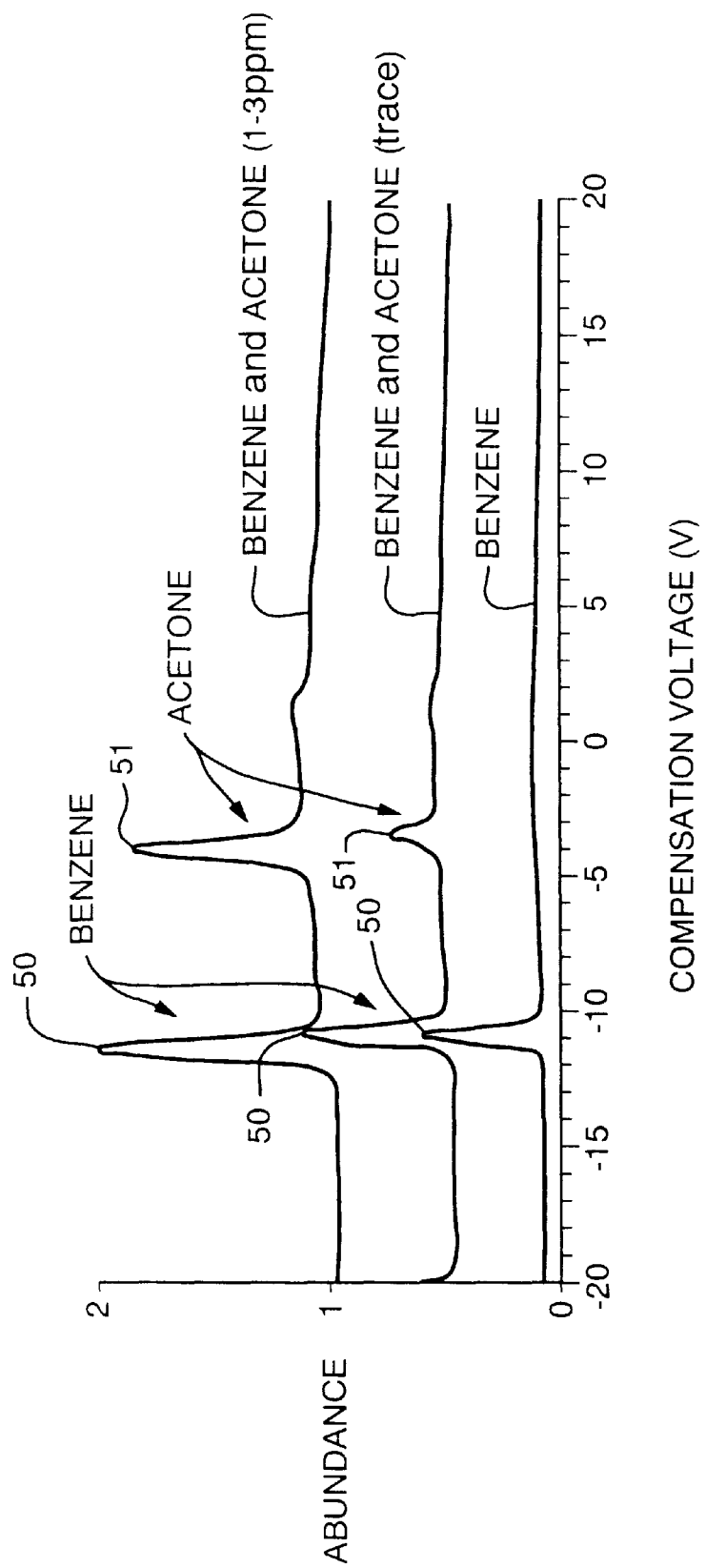
FIG. 9 is graphical representation demonstrating identification of individual chemicals from a mixture of benzene and acetone.

As shown in FIG. 9, identification of individual constituents of a mixture is demonstrated by the distinct Benzene peaks 50 and the acetone peaks 51.

Figure 10:
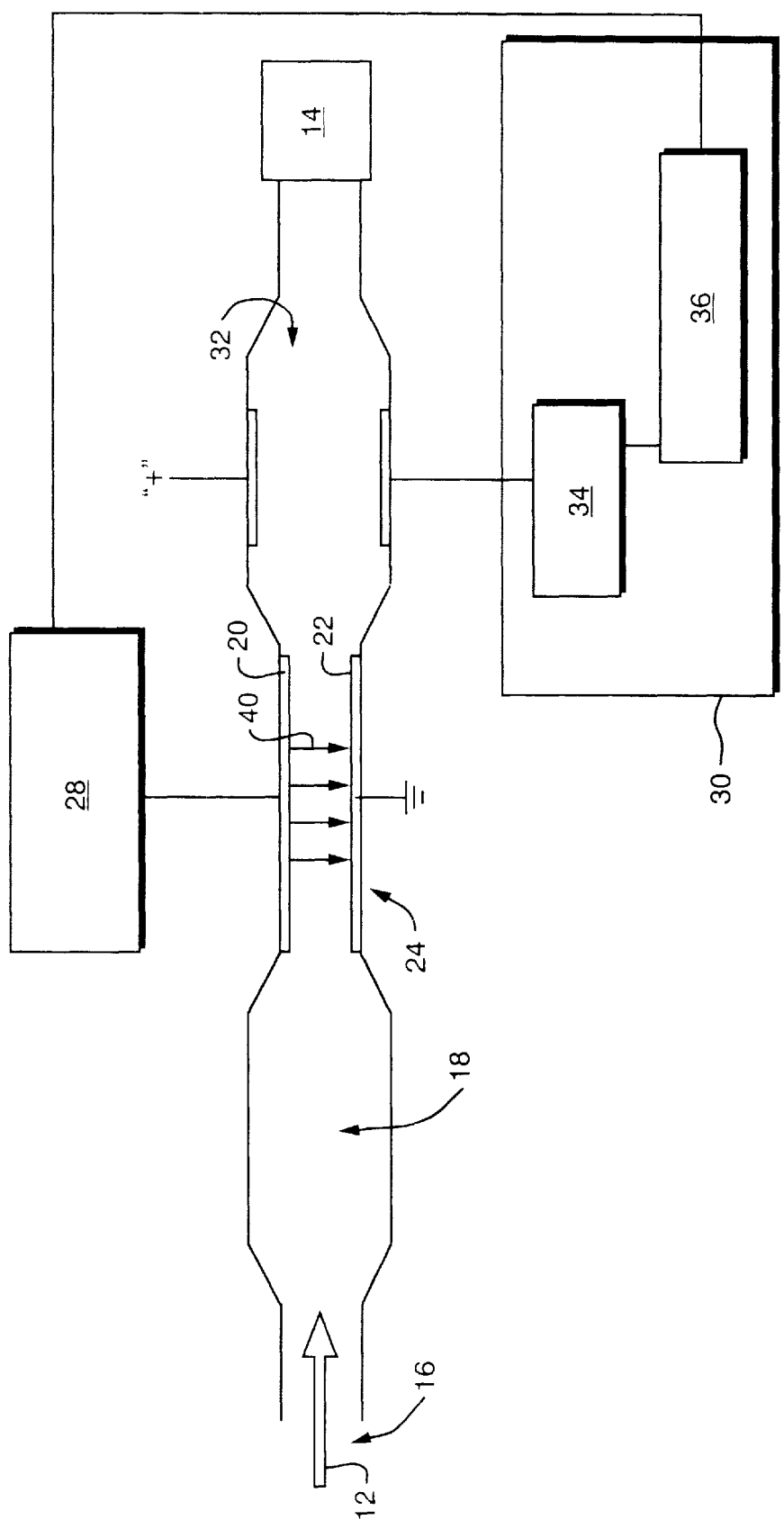
FIG. 10 is a schematic block diagram, similar to FIG. 1, in which the filter is not compensated by a bias voltage and the duty cycle of the periodic voltage is instead varied to control the flow of ions through the filter.

It has also been found that a compensation bias voltage is not necessary to detect a selected specie or species of ion. By varying the duty cycle of the asymmetric periodic voltage. applied to electrodes 20 and 22 of filter 24, FIG. 10, there is no need to apply a constant bias voltage to plate electrodes 20 and 22. Voltage generator 28, in response to control electronics 30 varies the duty cycle of asymmetric alternating electric field 40.

Figure 11:
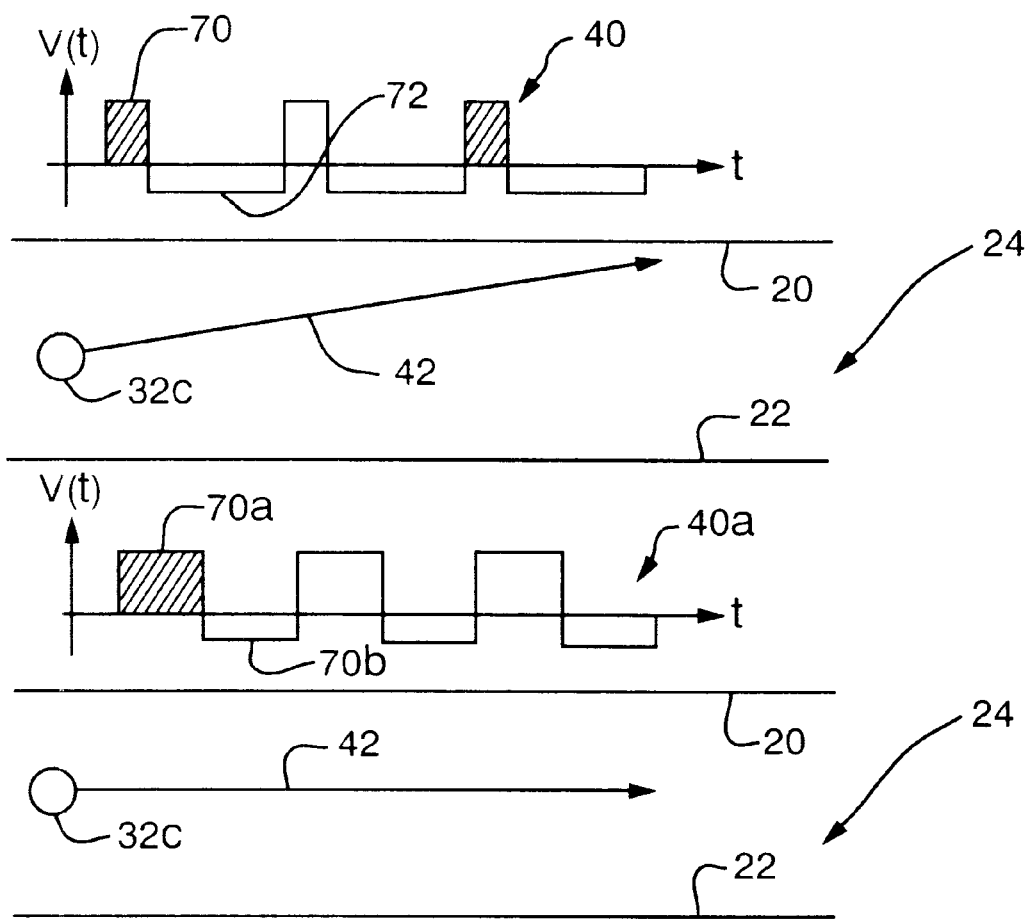
FIG. 11 is a graphical representation of an asymmetric periodic voltage having a varying duty cycle which is applied to the filter of FIG. 9 to filter selected ions without a bias voltage.

By varying the duty cycle of periodic electric field 40, FIG. 11, the path of selected ion 32c may be controlled. As an example, rather than a limitation, the duty cycle of field 40 may be one quarter: 25% high, peak 70, and 75% low, valley 72, and ion 38c approaches plate 20 to be neutralized. However, by varying the duty cycle of voltage 40a to 40%, peak 70a, ion 38c passes through plates 20 and 22 without being neutralized. Typically the duty cycle is variable from 10–50% high and 90–50% low. Accordingly, by varying the duty cycle of field 40, an ion's path may be controlled without the need of a bias voltage.

Figure 12:
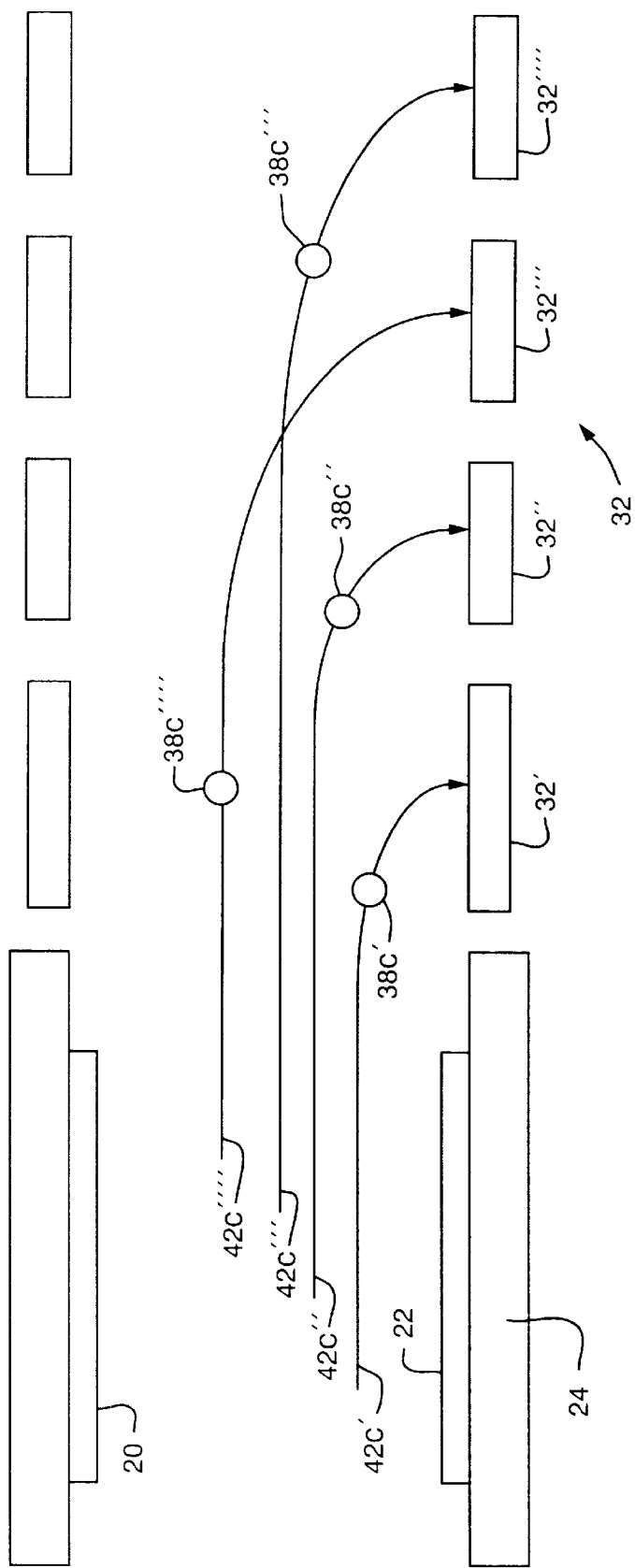
FIG. 12 is a schematic diagram of a filter and detector system in which the detector is segmented to spatially detect ions as they exit the filter.

To improve FAIM spectrometry resolution even further, detector 32, FIG. 12, may be segmented. Thus, as ions pass through filter 24 between filter electrodes 20 and 22, the individual ions 38c'–38c'''' may be detected spatially, the ions having their trajectories 42c'–42c'''' determined according to their size, charge and cross section. Thus detector segment 32' will have a concentration of one species of ion while detector segment 32'' will have a different, ion species concentration, increasing the spectrum resolution as each segment may detect a particular ion species.

Figure 13:
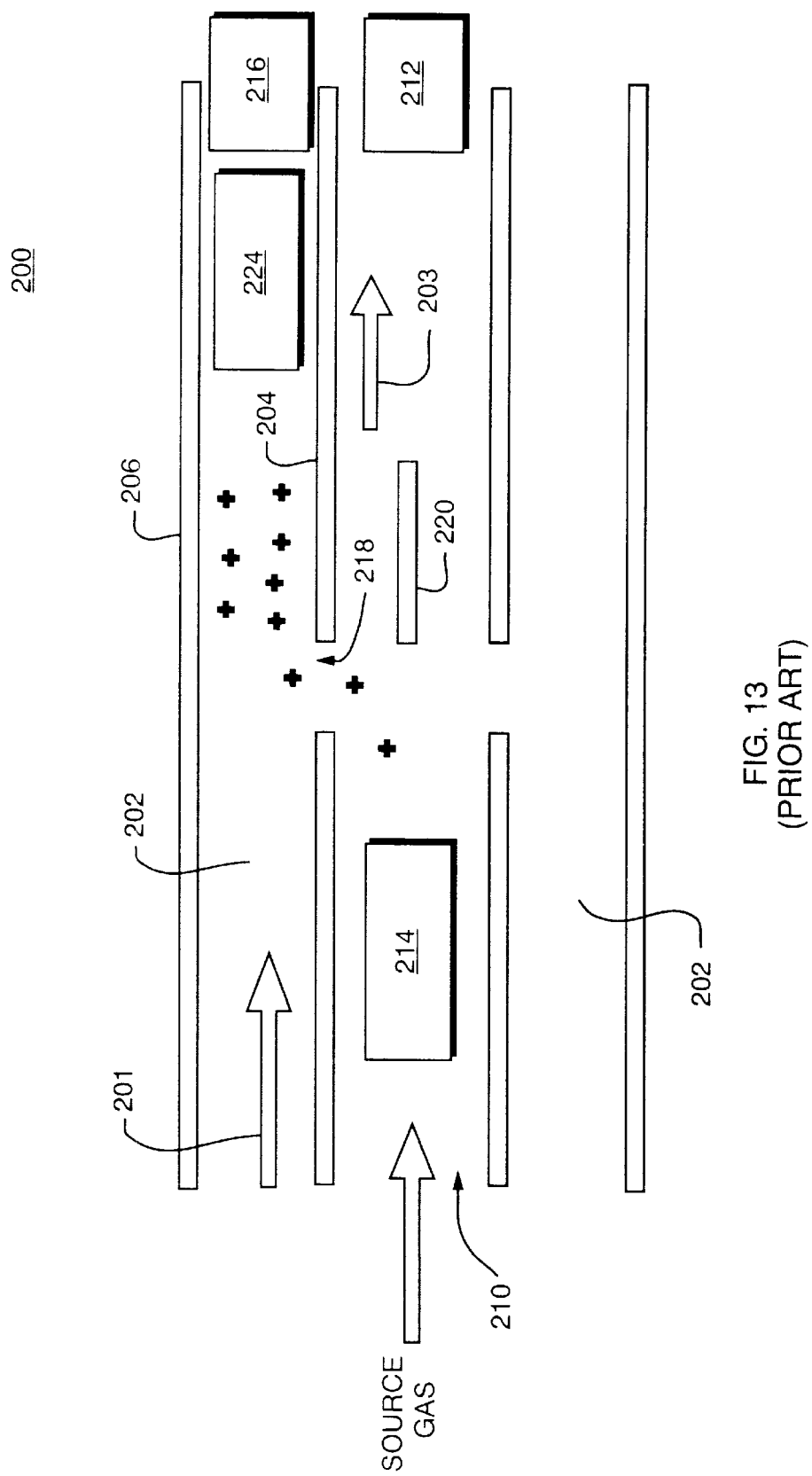
FIG. 13 is a schematic view of a typical prior art spectrometer.

One prior art ion mobility spectrometer 200, FIG. 13, (See U.S. Pat. No. 5,420,424) includes analytical gap 202 defined by the space between inner 204 and outer 206 longitudinal electrodes. Sample media, or a source gas is drawn through inlet 210 via the action of pump 212 and ionized by ionization source 214. A carrier gas is introduced via pump 216 into analytical gap 202. Ions generated by ionization source 214 travel through aperture 218 by the action of electrode 220 and into analytical gap 202 until they reach detector 224.

Such a structure requires two pumps 212 and 216, and separate flow paths 201 and 203 for the source gas and the carrier gas. Thus, prior art mobility spectrometer 200 cannot be made very small, and requires sufficient power to operate pumps 212 and 216.

In the subject invention, the need for pumps 212 and 216 is either eliminated or the pumps are made smaller, even micromachined pumps can be used, for example. Furthermore, separate flow paths for the source gas and the carrier gas are not required and clean filtered gas such as dehumidified air can be introduced to flow in a direction opposite the direction of ion travel to eliminate ion clustering and to improve (lower) the spectrometer's sensitivity to the effects of humidity.

Figure 14:
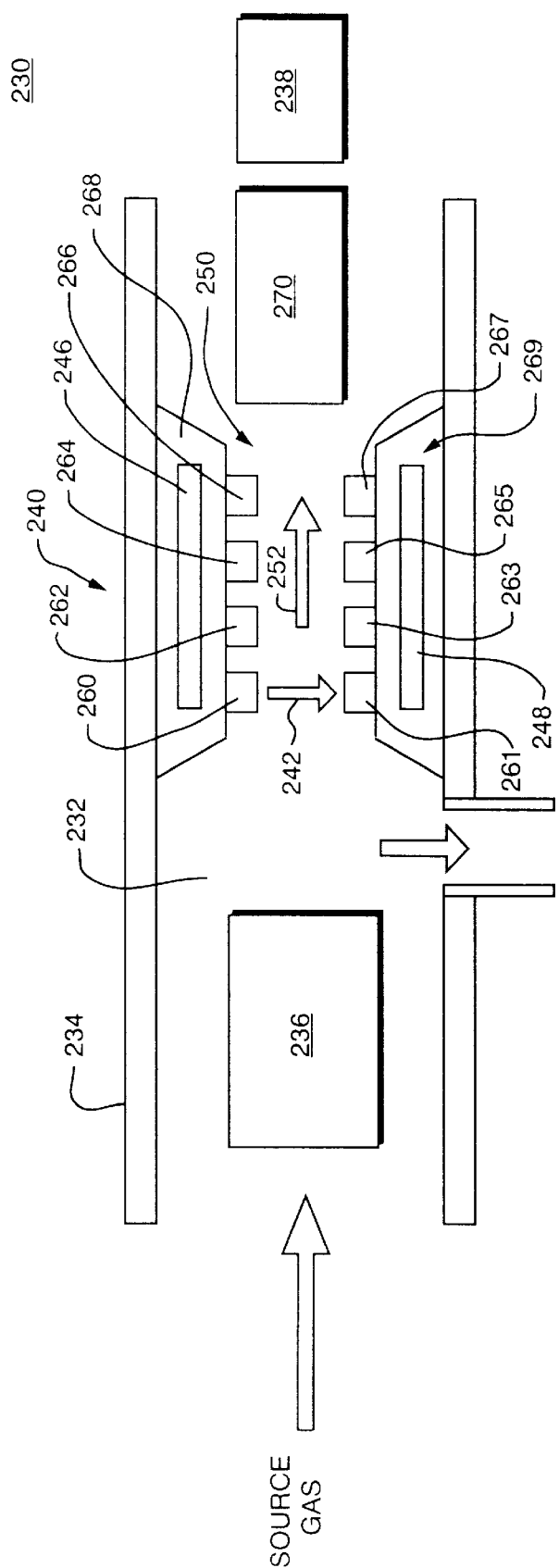
FIG. 14 is a schematic view of one embodiment of the longitudinal field driven ion mobility spectrometer of the subject invention.

Field asymmetric ion mobility spectrometer 230 according to this invention, FIG. 14, includes analytical gap 232 inside structure 234 which may be a round tube or a small flat housing with walls defining an enclosure. Ionization source 236 ionizes a sample media or gas driven into analytical gap 232 via the action of pump 238 which may be a micromachined pump with a flow rate of much less than the typically required 1–4 liters per minute of the prior art resulting in a power savings of between 1–5 watts over prior art spectrometers.

Ion filter 240 is disposed in analytical gap 232 downstream from ionization source 236 for creating an asymmetre electric field shown by vector 242 to filter ions generated by ionization source 236 as discussed supra.

Ion filter 240 typically includes a pair of spaced electrodes 248 and 246 connected to an electric controller which applies a biased voltage and an asymmetric periodic voltage to electrodes 246 and 248, see FIGS. 1–2.

Unique to spectrometer 230 is ion flow generator 250 for creating a longitudinal electric field as shown by vector 252. The strength of longitudinal electric field 252 can be constant in time or space or can vary with time and space and propels ions through asymmetric electric field 242.

In one embodiment, ion flow generator 250 includes discrete electrodes 260, 262, 264, and 266 insulated from electrode 246 and discrete electrodes 261, 263, 265 and 267 insulated from electrode 248 by insulating mediums 268 and 269. In one example, electrode 260 is at 1,000 volts, electrode 266 is at 10 volts and electrodes 262 and 264 are at 500 and 100 volts respectively, although these voltage levels may vary depending on the specific implementation of spectrometer 230. The voltages applied to electrodes 261, 263, 265, and 267 generally match the voltages applied to electrodes 260, 262, 264, and 266, respectively. There may be more or fewer electrodes opposing each other forming ion flow generator 250. Electrode pairs (260, 261), (262, 263), (264, 265), and (266, 267) can also each be a ring electrode as well as discrete planar electrodes.

In any case, the strength of longitudinal electric field 252 propels ions generated by ionization source 236 through asymmetric electric field 242 and towards detector 270 thus eliminating or reducing the flow rate and power requirements of pumps 212 and 216, FIG. 13 of the prior art.

Typically, detector 270 is positioned close to ion flow generator 250 and electrodes 260, 262, 264, 266, 261, 263, 265, and 267 preferably occupy more or less the same physical space as ion filter 240 electrodes 246 and 248 relative to analytical gap 232.

Figure 15:
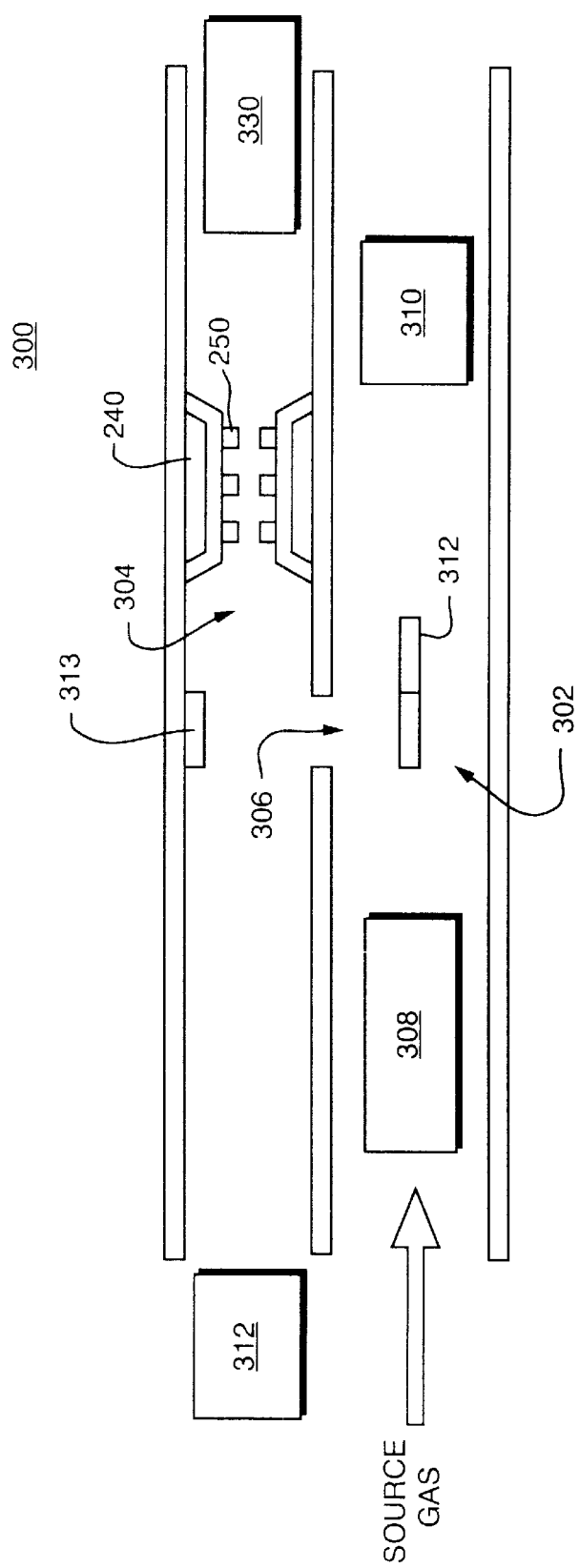
FIG. 15 is a schematic view of another embodiment of the longitudinal field driven ion mobility spectrometer of this invention.

In another embodiment, spectrometer 300, FIG. 15, includes structure which defines flow path 302 and analytical gap 304 with an opening 306 there between. Source gas is drawn into flow path 302 by pump 310 and ionized by ionization source 308. The ions are deflected through opening 306 and into analytical gap 304 by deflecting electrodes 312 and 313 where the electrodes of ion flow generator 250 and ion filter 240 are disposed. Ion flow generator 250 propels the ions through the asymmetric ion field created by filter 240 as discussed above. In this way, pump 312 need only supply a fairly low flow rate of dehumidified air into analytical gap 304 and no carrier gas flow is required as taught by the prior art.

Figure 16:
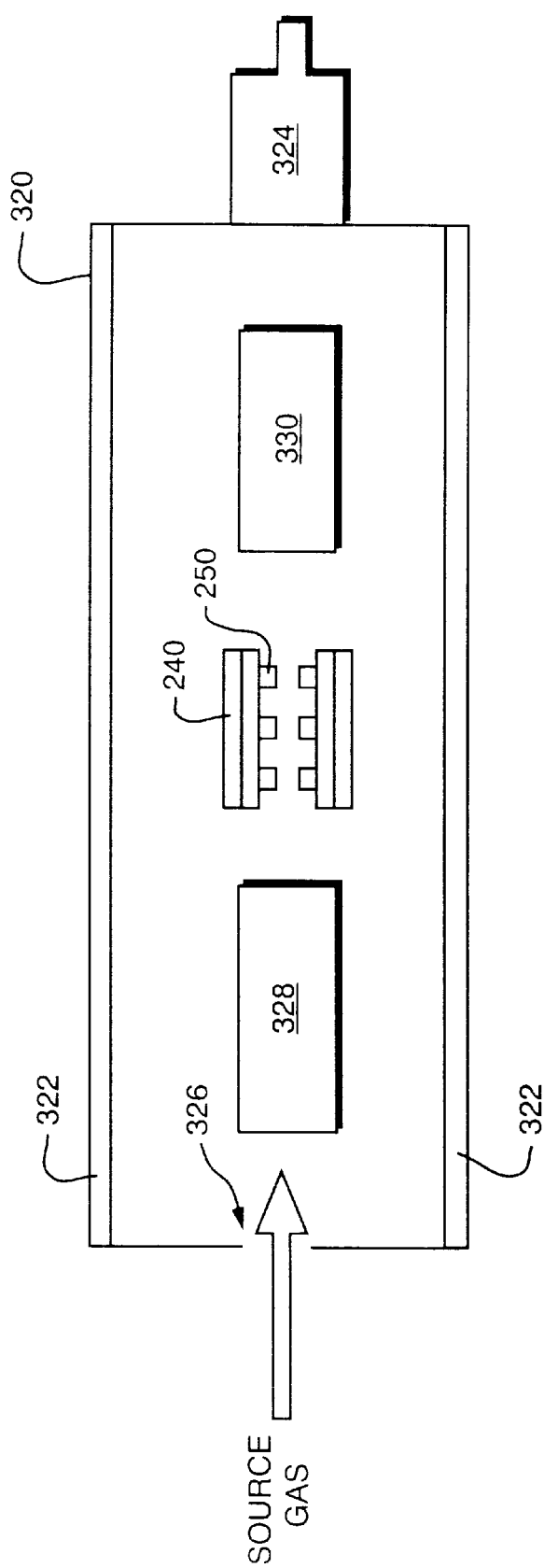
FIG. 16 is a schematic view of another embodiment of the longitudinal field driven ion mobility spectrometer of this invention.

In another embodiment, a desiccant 322, FIG. 16, is provided in housing 320 and small pump 324 is the only pump required to draw source gas into housing 320 through small orifice 326. Ionization source 328 produces ions which travel through filter 240 aided by the longitudinal electric field created by ion flow generator 250 positioned proximate detector 330.

Figure 17:
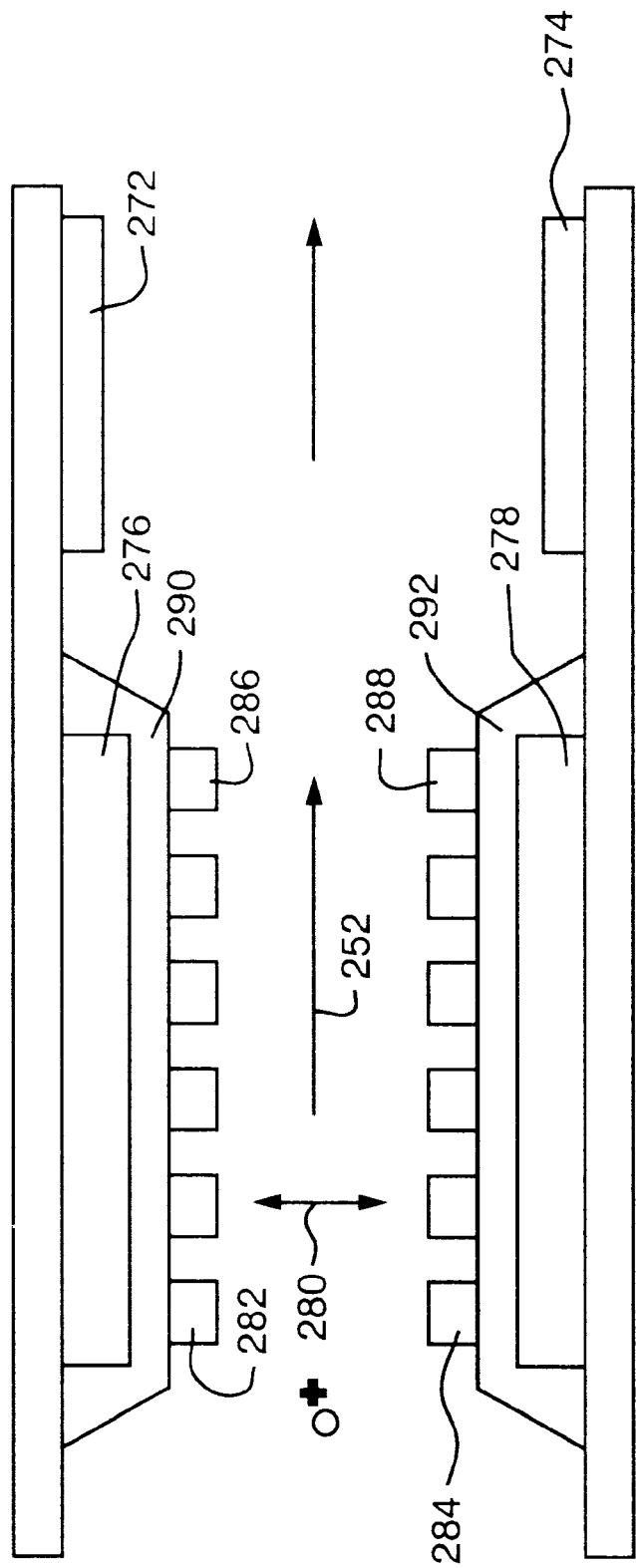
FIG. 17 is a schematic view of the ion filter, detector, and ion flow generator portion of the spectrometer of this invention.

In one embodiment detector 270, FIG. 14, includes spaced electrodes 272, 274, FIG. 17, similar in construction to electrodes 33 and 35, FIG. 1. The ion filter of FIG. 17 includes spaced electrodes 276 and 278 for creating transverse electric field 280. The ion flow generator includes spaced discrete electrodes as shown for electrodes 282 and 284 and electrodes 286 and 288. Electrodes 282 and 284 may be at 1000 volts and electrodes 286 and 288 may be at 0 volts. Insulating medium 290 and 292 insulates electrodes 282, 284, 286, and 288 with respect to electrodes 276 and 278. Electrode pairs (282, 284) through (286, 288) or more could also be ring electrodes.

Figure 18:
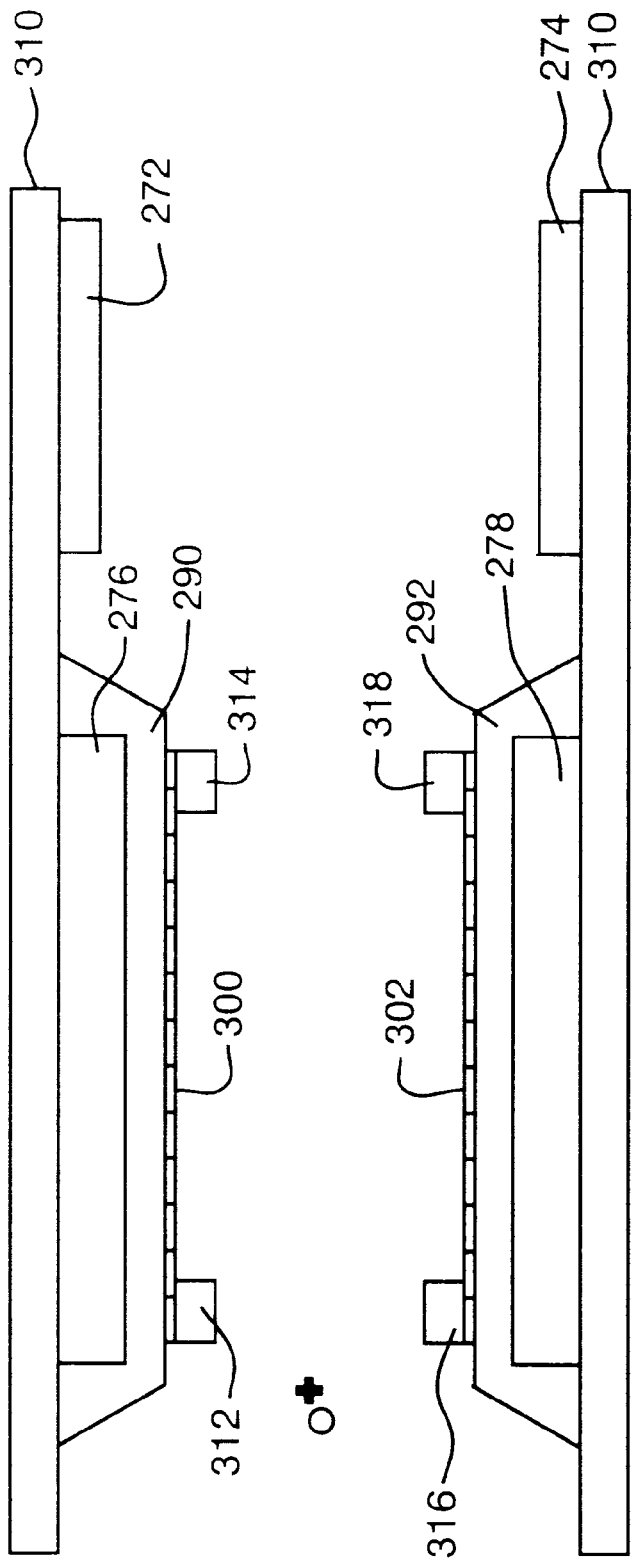
FIG. 18 is a schematic view of another embodiment of the ion filter, detector, and ion flow generator portion of a spectrometer according to this invention.

In another embodiment, FIG. 18, the ion filter includes spaced resistive layers 300 and 302 insulated from electrodes 276 and 278 on Pyrex substrate 310 by insulating medium 290 and 292, for example, a low temperature oxide material.

Resistive layers 300 and 302 may be a resistive ceramic material deposited on insulating layers 290 and 292, respectively. Terminal electrodes 312, 314, 316 and 318 make contact with each resistive layer to apply a voltage drop across each resistive layer to generate the longitudinal electric field. Thus, electrodes 312 and 316 may be at 1000 volts while electrodes 314 and 318 may be at 0 volts. This embodiment can be extended to a cylindrical geometry by making electrodes 312 and 316 a ring electrode, electrodes 314 and 318 a ring electrode, and resistive layers 300 and 302 an open cylinder.

Figure 19:
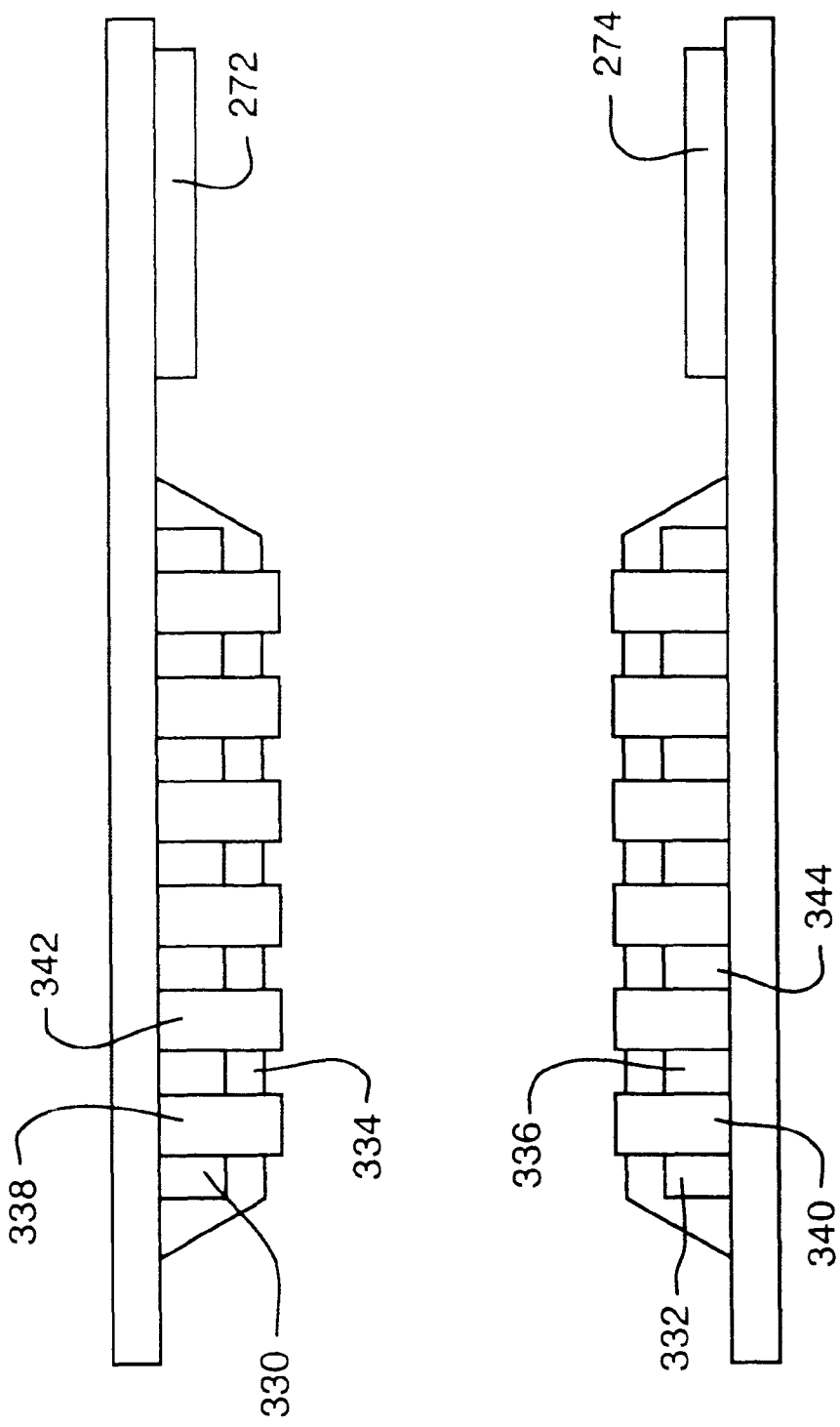
FIG. 19 is a schematic view of another embodiment of the ion filter, detector, and ion flow generator portion of a spectrometer according to this invention.

In still another embodiment, FIG. 19, the ion filter includes a plurality of high frequency, high voltage electrodes 330, 332, 334 and 336 connected to an electric controller (see FIG. 1) which applies an asymmetric periodic voltage to create an ion filtering electric field and the ion flow generator includes a second plurality of discrete electrodes 338, 340, 342 and 344 dispersed among but insulated from the discrete electrodes of the ion filter as shown and connected to a voltage source which applies a potential gradient across them to generate an ion propelling electric field which is in a direction transverse to the ion filtering electric field.

Figure 20:
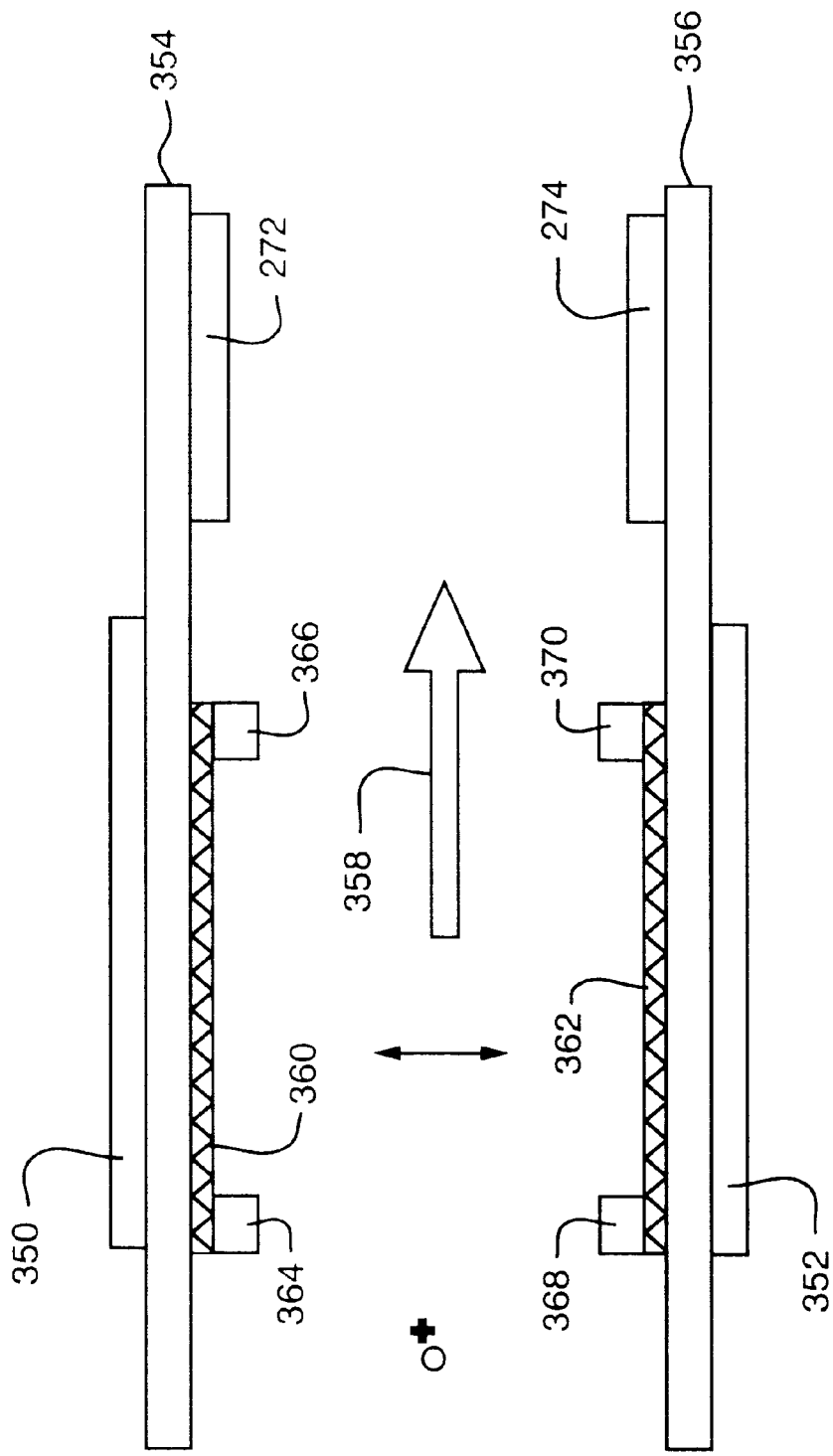
FIG. 20 is a schematic view of another embodiment of the ion filter, detector, and ion flow generator portion of a spectrometer according to this invention.

In still another embodiment, FIG. 20, high frequency electrodes 350, 352 which provide the asymmetric ion filtering electric field are disposed on the outside of walls 354 and 356 made of an insulative material such as PYREX which define analytical gap 358. Resistive layers 360 and 362 may be a resistive ceramic material deposited on the inside of walls insulating walls 354 and 356, respectively. Terminal electrodes 364 and 366, and 368 and 370 make contact with each resistive layer is shown to apply a voltage drop across each resistive layer to generate the ion propelling longitudinal electric field. Thus, electrodes 364 and 368 may each be at 1000 volts while electrodes 366 and 370 are at 0 volts.

Figure 21:
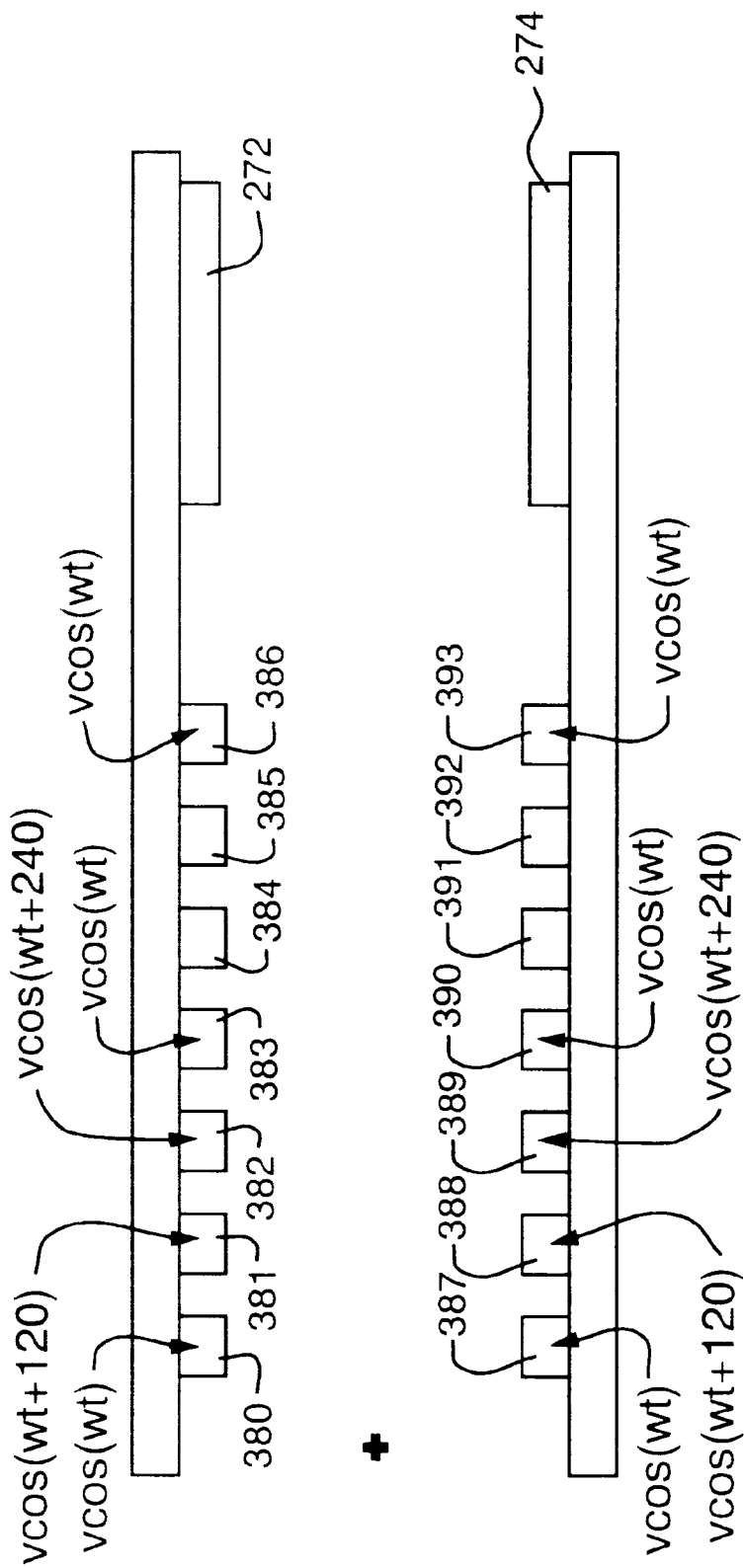
FIG. 21 is a schematic view of another embodiment of the ion filter, detector, and ion flow generator portion of a spectrometer according to this invention.

In the design shown in FIG. 21, discrete electrodes 380–386 and 387–394 produce an electrical field with both transverse and longitudinal components to both filter and propel the ions. A travelling wave voltage of the form $$V \cos(wt-kz) \qquad 1$$

where $k = 2\pi/\lambda$ is the wave number and w is the radian frequency has an associated electric field with both transverse and longitudinal components. For a planar system, each succeeding set of opposing electrodes is excited by a voltage source at a fixed phase difference from the voltage source applied to the adjacent set of opposing electrodes.

Thus, electrodes 380 and 387 are excited with a voltage of $v \cos(wt)$ while electrodes 381 and 388 are excited with a voltage of $v \cos(wt+120)$ and so on as shown in FIG. 21. Travelling wave voltages require polyphase voltage excitations, the simplest being a two phase excitation. So, a two conductor ribbon could also be wound around a duct defining the analytical gap with one conductor excited at $v \cos(wt)$ and the other conductor excited at $v \sin(wt)$. Three phase excitations could be incorporated if the conductor ribbon or tape had three conductors.

The subject designs lend themselves well to the use of an electrospray ionization source nozzle because certain electrodes can function both as the source for the longitudinal electrical field which transports the ions towards the detector electrodes and as the electrodes which create a fine spray of solvent droplets for ionizing the source gas or sample medium.

Thus, in accordance with this invention, pumps 216 and 212, FIG. 13 of the prior art are either eliminated or at least reduced in size and have lower flow rate and power requirements. By the incorporation of an ion flow generator which creates a longitudinal electric field in the direction of the intended ion travel, the ions are propelled to the detector and through the transversely directed asymmetric electric field which acts as an ion filter. In the preferred embodiment, a pump is not required to draw the ionized gas species through the spectrometer drift tube for analysis. Instead, a longitudinal electric field applied along the length of the drift tube can be used to propel the ions down the drift tube through the ion filter to a detector. By eliminating the high flow rate (1–4 liters per minute) pumps used in prior art spectrometers, a significant reduction in power consumption, size, and cost can be realized leading to a truly miniaturized spectrometer on a chip.

A second benefit of this design is that a flow of clean filtered air can be applied in a direction opposite the direction of the motion of the ions. In this way, any neutrals in the sample gas which were not ionized are deflected away and do not enter the ion analysis region. The result is the elimination of ion clustering problems and the humidity sensitivity of the sensor. Because the flow rates are low, it is possible to incorporate integrated micromachine pumps.

Since only the ions need enter the analysis region, no gas flow is required in the ion filter and detector region. Molecular sieves can be located close to the entrance of this region in order to absorb any neutral molecules in the analysis region and prevent clustering. A separate source of air flow delivered by a pump in the ion filter (analyzer) region is not required in contrast to the prior art which incorporated high flow rate pumps which consumed a relatively large amount of power (1–5 watts) and which added size to the system and/or which could fail. In subject invention, a flow of neutral gas in the same direction as the ion species generated from the sample gas to be analyzed is not required. Instead a flow gas in the opposite direction of the ion flow direction can be applied to keep the ion filter region free of unwanted neutrals and moisture. A higher gas flow rate through the ion filter (drift tube) is not required. Instead, the ions are drawn through the ion filter (drift tube) along the z axis by a longitudinal electric field produced by a small potential gradient in the z direction. In the design shown, FIG. 17, only a low volume flow in the direction of the longitudinal electric field as shown by vector 252 is required to bring the ions proximate to electrodes 282 and 284. No gas flow is required in the ion filter and detector region due to longitudinal electric field 252. Also, if required, a low flow volume of clean filtered air can be provided in a direction opposite the longitudinal electric field to keep the ion filter and detector region free of neutrals. A resistive divider circuit provides a potential gradient across electrodes 282, 284, so that for example, electrodes 282 and 284 are at 1000 volts while electrodes 286 and 288 are at 0 volts. In the design shown in FIG. 19, all the high frequency electrodes 330, 332, etc. are electrically tied together while the longitudinal field producing electrodes 338, 340 etc. have a potential gradient dropped across them. In one embodiment, the voltages applied to the electrodes can be alternated so that first a voltage is applied to generate the transverse electric field and then a voltage is applied to other electrodes to generate the longitudinal electric field.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. An asymmetric field ion mobility spectrometer comprising:

an ionization source for ionizing a sample media and creating ions;

an analytical gap;

an ion filter disposed in the analytical gap downstream from the ionization source, and including a pair of spaced electrodes for creating an asymmetric electric field to filter the ions;

an ion flow generator including a plurality of spaced discrete electrodes insulated from the pair of spaced electrodes for creating an electric field transverse to the asymmetric electric field for propelling ions through the asymmetric electric field; and an ion detector for sensing ions not filtered by the ion filter.

2. The spectrometer for claim 1 in which the ion detector is proximate the ion flow generator.

3. The spectrometer of claim 2 in which the ionization source is a radiation source.

4. The spectrometer of claim 1 in which the ionization source includes an ultraviolet lamp.

5. The spectrometer of claim 1 in which the ionization source includes a corona discharge device.

6. The spectrometer of claim 1 in which the ionization source includes an electrospray nozzle.

7. The spectrometer of claim 1 in which the ion filter is connected to an electric controller for applying a bias voltage and an asymmetric periodic voltage to the ion filter.

8. The spectrometer of claim 1 in which the ion flow generator includes spaced resistive layers and a voltage applied along each layer to create a longitudinal electric field.

9. The spectrometer of claim 1 in which the ion filter includes a first plurality of discrete electrodes electrically connected to an electric controller which applies an asymmetric periodic voltage to the first plurality of discrete electrodes and in which the ion flow generator includes a second plurality of discrete electrodes dispersed among the first plurality of discrete electrodes connected to a voltage source which applies a potential gradient along the second plurality of discrete electrodes.

10. The spectrometer of claim 1 in which the analytical gap is enclosed by a housing, the ion filter includes electrodes on an outside surface of the housing and the ion flow generator includes resistive layers on an inside surface of the housing and a voltage is applied along each layer to create a longitudinal electric field.

11. The spectrometer of claim 1 in which the ion filter and the ion flow generator are combined and include a series of discrete conductive elements each excited by a voltage source at a different phase.

12. The spectrometer of claim 1 in which the ion filter is connected to an electric controller for applying a traveling wave voltage.

13. An asymmetric field ion mobility spectrometer comprising:

an ionization source for ionizing a sample media and creating ions;

an analytical gap enclosed by a housing;

an ion filter disposed in the analytical gap downstream from the ionization source, and including electrodes on an inside surface of the housing for creating an asymmetric electric field to filter the ions;

an ion flow generator including electrodes proximate but insulated with respect to the ion filter electrodes for creating an electric field transverse to the asymmetric electric field for propelling ions through the asymmetric electric field; and an ion detector for sensing ions not filtered by the ion filter.

14. The spectrometer of claim 13 in which the ion detector includes electrodes on an inside surface of the housing proximate the ion filter and the ion flow generator.

* * * * *